(12) United States Patent
Klapproth et al.

(10) Patent No.: US 11,952,614 B2
(45) Date of Patent: *Apr. 9, 2024

(54) BEAD BEATING TUBE AND METHOD FOR EXTRACTING DEOXYRIBONUCLEIC ACID AND/OR RIBONUCLEIC ACID FROM MICROORGANISMS

(71) Applicant: SAFEGUARD BIOSYSTEMS HOLDINGS LTD., London (GB)

(72) Inventors: Holger Klapproth, Freiburg (DE); Nicolaas Smit, Welland (CA)

(73) Assignee: Safeguard Biosystems Holdings Ltd., London (GB)

( * ) Notice: Subject to any disclaimer, the term of this patent is extended or adjusted under 35 U.S.C. 154(b) by 296 days.

This patent is subject to a terminal disclaimer.

(21) Appl. No.: 17/147,826

(22) Filed: Jan. 13, 2021

(65) Prior Publication Data

US 2021/0139952 A1    May 13, 2021

Related U.S. Application Data

(60) Division of application No. 16/023,492, filed on Jun. 29, 2018, now abandoned, which is a division of application No. 15/432,157, filed on Feb. 14, 2017, now Pat. No. 10,036,054, which is a continuation of application No. PCT/EP2017/051902, filed on Jan. 30, 2017.

(30) Foreign Application Priority Data

Jan. 30, 2016 (EP) .................................. 16153540

(51) Int. Cl.
| | |
|---|---|
| C12Q 1/68 | (2018.01) |
| B01L 3/00 | (2006.01) |
| C12M 1/00 | (2006.01) |
| C12Q 1/6806 | (2018.01) |
| C12Q 1/6874 | (2018.01) |
| G01N 35/00 | (2006.01) |

(52) U.S. Cl.
CPC .......... *C12Q 1/6806* (2013.01); *B01L 3/5082* (2013.01); *C12M 47/06* (2013.01); *C12Q 1/6874* (2013.01); *B01L 2300/16* (2013.01); *G01N 2035/00524* (2013.01)

(58) Field of Classification Search
CPC .... C12Q 1/6806; C12Q 1/6874; C12Q 1/689; C12Q 1/6895; C12Q 2563/149; C12M 47/06; B01L 3/5082; B01L 2300/16; G01N 2035/00524
See application file for complete search history.

(56) References Cited

U.S. PATENT DOCUMENTS

| | | | |
|---|---|---|---|
| 10,036,054 B2 | 7/2018 | Klapproth et al. | |
| 11,667,884 B2 | 6/2023 | Klapproth et al. | |
| 2004/0076990 A1 | 4/2004 | Picard et al. | |
| 2010/0137575 A1 | 6/2010 | Connolly et al. | |
| 2011/0245094 A1 | 10/2011 | Washburn et al. | |
| 2011/0308790 A1 | 12/2011 | Strapoc et al. | |
| 2012/0094353 A1 | 4/2012 | Baelum et al. | |
| 2012/0100546 A1 | 4/2012 | Lowery, Jr. et al. | |
| 2013/0323815 A1* | 12/2013 | Gundling ................. | C12N 1/06 435/270 |
| 2014/0171360 A1 | 6/2014 | Polo Pozo et al. | |
| 2017/0218356 A1 | 8/2017 | Klapproth et al. | |
| 2021/0284951 A1 | 9/2021 | Klapproth et al. | |

FOREIGN PATENT DOCUMENTS

| | | |
|---|---|---|
| CN | 101163802 A2 | 4/2008 |
| CN | 10441074 A | 3/2015 |
| EP | 1574583 | 9/2005 |
| JP | 2008/154521 | 7/2008 |
| JP | 2008/298615 | 12/2008 |
| JP | 2010/537650 A1 | 12/2010 |
| JP | 2015530092 | 10/2015 |
| WO | 95/28409 A1 | 10/1995 |
| WO | 2005/073377 A1 | 8/2005 |
| WO | 2010/065420 A2 | 6/2010 |
| WO | 2010/086099 | 8/2010 |
| WO | 2011/034621 A2 | 3/2011 |
| WO | 2012/027302 A2 | 3/2012 |
| WO | 2012/050787 A1 | 4/2012 |
| WO | 2012/054638 A2 | 4/2012 |
| WO | 2012/2054975 | 5/2012 |
| WO | 2013/036603 A1 | 3/2013 |
| WO | 2013/091102 A1 | 6/2013 |
| WO | 2013/096799 A1 | 6/2013 |
| WO | 2015/003060 | 1/2015 |
| WO | 2017/129814 A1 | 8/2017 |

(Continued)

OTHER PUBLICATIONS

European Search Report dated Feb. 21, 2022 in connection with application No. 21203244.5.
Examination report dated Feb. 17, 2022 in connection with Australian application No. 2018211530.
Examination report dated Sep. 20, 2021 in connection with Indian application No. 201837027128.
English translation of Office Action dated Jul. 7, 2022 in connection with Chinese application No. 201780008892.1.
Asahida et al., 1996 "Tissue Preservation and Total DNA Extraction from Fish Stored at Ambient Temperature Using Buffers Containing High Concentration of Urea," Fisher Science 62(5):727-730.
Gelhaus et al., 1995 "DNA extraction from urea-preserved blood or blood clots for use in PCR," Trends in Genetics 11(2):41.
Yongsheng, 2015 "Production Technology of Glutathione," 1:141-142.

(Continued)

*Primary Examiner* — Kenneth R Horlick
(74) *Attorney, Agent, or Firm* — Biospark Intellectual Property Law

(57) ABSTRACT

The present disclosure provides improved methods for bead beating and a bead beating system useful therefor. The bead beating system comprises a sample tube, beads, and a dry blocking agent, and methods for using the bead beating system to extract nucleic acids from cells containing the nucleic acids.

28 Claims, 9 Drawing Sheets

(56) References Cited

FOREIGN PATENT DOCUMENTS

WO    2018/138363    8/2018

OTHER PUBLICATIONS

Figure 1:
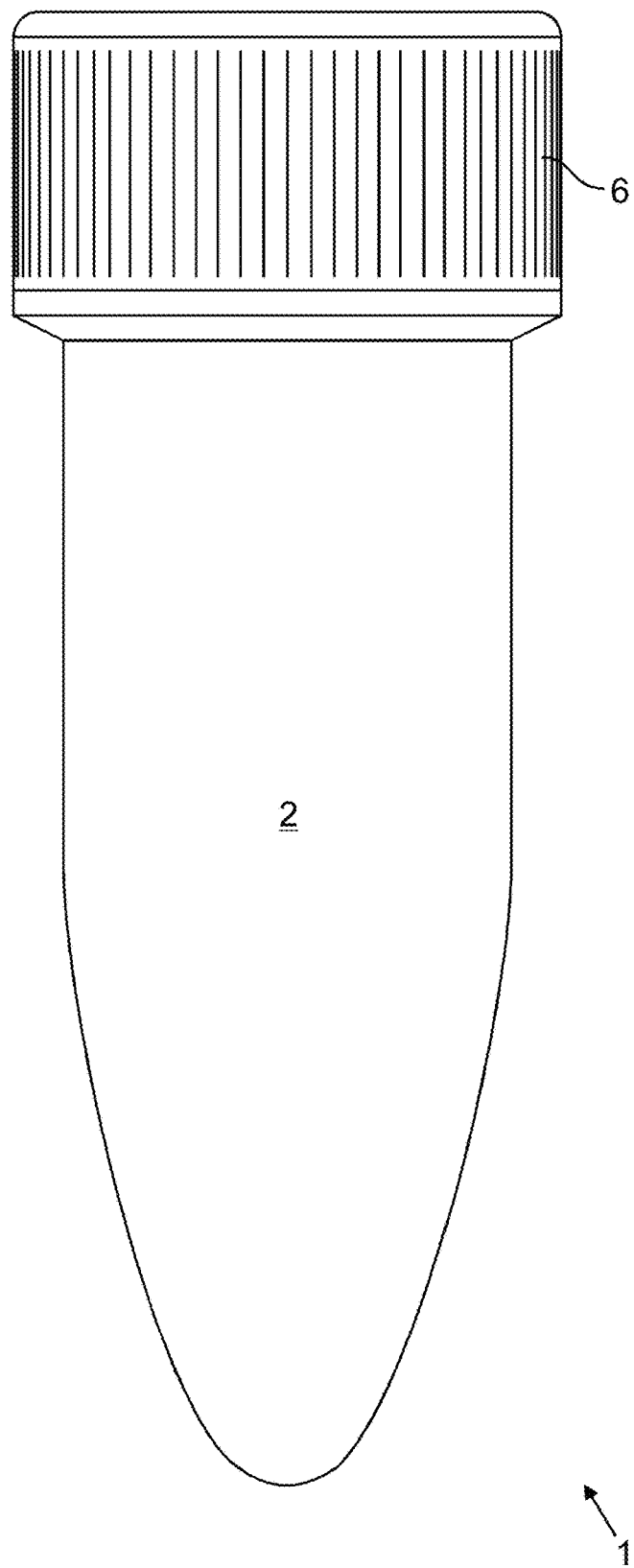

Extended European Search Report dated Jul. 18, 2016 in connection with European application No. 16153540.6.
Notification of Transmittal of the International Search Report and the Written Opinion of the International Searching Authority, or the Declaration, International Search Report, and Written Opinion of the International Searching Authority dated Apr. 18, 2017 in connection with PCT/EP2017/051902.
Invitation to Pay Additional Fees and, Where Applicable, Protest Fee with Communication Relating to the Results of the Partial International Search, dated Mar. 16, 2018 in connection with PCT International Application No. PCT/EP2018/052173.
Bolano et al., 2001, "Rapid methods to extract DNA and RNA from *Cryptococcus neoformans*," FEMS Yeast Research 1:221-224.
Cullen and Hirsch, 1998, "Simple and Rapid Method for Direct Extraction of Microbial DNA from Soil for PCR," Soil Biol. Biochem. 30(8/9):983-993.
Eshoo et al. 2012, "Direct Molecular Detection and Genotyping of *Borrelia burgdorferi* from Whole Blood of Patients with Early Lyme Disease," PLoS One 7(5):e36825.
Ferguson et al., 2016, "Pilot study of a rapid and minimally instrumented sputum sample preparation method for molecular diagnosis of tuberculosis," Sci Rep. 6:19541.
Fujimoto et al., 2004, "Optimal Bacterial DNA Isolation Method Using Bead-Beating Technique," Memoirs Kyushu Univ. Dep. Of Health Scis. Of Medical Sch. 3:33-38.
Gkatzionis et al., 2014, "Diversity and activities of yeasts from different parts of a Stilton cheese," International Journal of Food Microbiology 177:109-116.
Ho et al., 2013, "Selection of elite microalgae for biodiesel production in tropical conditions using a standardized platform," Bioresource Technology 147:135-142.
Hossain Ripon et al., 2011, "Comparison of Three Different Methods of Genomic DNA Extraction from Gram Positive and Gram Negative Bacteria," J. Expt. Biosci. 2(1):55-60.
Jaffe et al., 2000, "Rapid Extraction from and Direct Identification in Clinical Samples of Methicillin-Resistant *Staphylococci* Using the PCR," Journal of Clinical Microbiology, 38(9):3407-3412.
Laffler et al., 2013, "Enhanced Diagnostic Yields of Bacteremia and Candidemia in Blood Specimens by PCR-Electrospray Ionization Mass Spectrometry," Journal of Clinical Microbiology, 51(11):3535-3541.
Moeller et al., 2013, "SIV-Induced Instability of the Chimpanzee Gut Microbiome," Cell Host & Microbe 14:340-345.
Nakashima et al., 2007, "Diversity of Phytases in the Rumen," Microbial Ecology 53:82-88.
Odumeru et al., 2001 "Use of the bead beater for preparation of *Mycobacterium paratuberculosis* template DNA in milk," The Canadian Journal of Veterinary Research 65:201-205.
Pathak et al., 2007, "Lysis of tubercle bacilli in fresh and stored sputum specimens: implications for diagnosing tuberculosis in stored and paucibacillary specimens by PCR," BMC Microbiology 7:83.
"Product Note: Benchmark Bead Beating Guide", ABC Scientific, downloaded from the internet on Jan. 25, 2016.
Thevaranjan, 2013 "DNA Isolation from Nasal Washes," Bowdish Lab, McMaster University.
Tito et al., 2015, "Choice of DNA extraction protocols from Gram negative and positive bacteria and directly from the soil," African Journal of Microbiology Research, 9(12):863-871.
"UltraClean® Microbial RNA Isolation Kit Instruction Manual," version 111315, MO BIO Laboratories, downloaded from the internet on Apr. 5, 2016.
Wang et al., 2011, "Characterization of a green microalga UTEX 2219-4: Effects of photosynthesis and osmotic stress on oil body formation," Botanical Studies 52:305-312.
Wesolowska-Andersen et al., 2014, "Choice of bacterial DNA extraction method from fecal material influences community structure as evaluated by metagenomic analysis," Microbiome, 2(19):1-11.
Widmer et al., 2001, "Assessing soil biological characteristics: a comparison of bulk soil community DNA-, PLFA-, and Biolog™-analysis," Soil Biology & Biochemistry 33:1029-1036.
Whelan, 2014, "Isolation of DNA from Clinical Samples (Genomic Prep")," Surette Lab, McMaster University.
Yu and Morrison, 2004, "Improved extraction of PCR-quality community DNA from digesta and fecal samples," BioTechniques 36:808-812.
First Examination Report dated May 30, 2019 in connection with New Zealand application No. 744436.
Notification Concerning Transmittal of Copy of International Preliminary Report on Patentability, International Preliminary Report on Patentability, Written Opinion of the International Searching Authority dated Aug. 8, 2019 in connection with PCT/EP2018/052173.
Gillespie et al., 2005, "Simultaneous Detection of Mastitis Pathogens, *Staphylococcus aureus, Streptococcus uberis*, and *Streptococcus agalactiae* by Multiplex Real-Time Polymerase Chain Reaction," J. Dairy Sci., 88:3510-3518, XP026956722.
Gomez et al., 2011, "Rapid DNA extraction for specific detection and quantitation of *Mycobacterium tuberculosis* DNA in sputum specimens using taqman assays," Tuberculosis (Edinb), 91S1:S43-S48, doi:10.1016/j.tube.2011.10.009.
Shreiner et al., 1973, "Pseudothrombocytopenia: Manifestation of a New Type of Platelet Agglutinin," Blood, 42(4):541-549.
Ripamonti M et al., 1984, "Urea, creatinine, and glucose determined in plasma and whole blood by differential pH technique." Clinical chemistry. 30(4):556-559.
Further Examination report dated Feb. 14, 2020 in connection with New Zealand application No. 744436.
Bacconi et al., 2014, "Improved Sensitivity for Molecular Detection of Bacterial and Candida Infections in Blood," Journal of Clinical Microbiology 52(9):3164-3174.

* cited by examiner

US 11,952,614 B2

BEAD BEATING TUBE AND METHOD FOR EXTRACTING DEOXYRIBONUCLEIC ACID AND/OR RIBONUCLEIC ACID FROM MICROORGANISMS

This application is a division of U.S. application Ser. No. 16/023,492, filed Jun. 29, 2018, which is a division of U.S. application Ser. No. 15/432,157, filed Feb. 14, 2017, now U.S. Pat. No. 10,036,054, which is a continuation of PCT application no. PCT/EP2017/051902, filed Jan. 30, 2017, which claims the priority benefit of European patent application no. EP16153540.6, filed on Jan. 30, 2016, the contents of each of which are incorporated by reference in their entireties.

1. BACKGROUND

Genetic testing and diagnosis of infectious diseases play an important role in the field of clinical microbiology. To overcome the bias and limitations inherent with culture-based methodologies, genetic testing is being increasingly used to detect microorganisms contained in a sample. In order that such genetic testing can be performed, cells need to be lysed to allow extraction of the DNA and/or the RNA from the microorganisms in a concentration as high as possible.

Zhongtang Yu et al., 2004, "Improved extraction of PCR-quality community DNA from digesta and fecal samples," BioTechniques, Vol. 36(5):808-812, describe a method for isolating DNA from digesta and fecal samples. In the method, 0.25 g of a sample fluid taken from a cow's gastro-intestinal system, which is assumed to contain microorganisms, namely bacteria, is first of all mixed with 1 mL of a buffer containing 500 mM sodium chloride, 50 mM Tris hydrochloride, pH 8.0, 50 mM ethylenediaminetetraacetic acid, and 4% sodium dodecyl sulfate. Moreover, 0.4 g sterile zirconia beads are introduced in the sample fluid. The mixture thus obtained is subsequently oscillated by means of a Mini-BeadBeater™ in a sample tube for three minutes such that the beads destroy the cell walls of the microorganisms. In this process, the DNA contained in the cells is released. The buffer also serves to protect the DNA from degradation by DNases which are contained in the sample fluid. After performing the bead beating, impurities are removed from the sample by precipitation with ammonium acetate. The nucleic acids are obtained by precipitation with isopropanol. In a further method step the DNA is digested sequentially with RNase and Proteinase K and subsequently purified by means of a column.

The method has the disadvantage that it is relatively complex. Since the sample fluid is diluted by the adding of the buffer, the DNA concentration in the sample decreases. Therefore, the method allows only a limited detection accuracy and sensitivity.

Thus, there is a need for improved devices and methods for lysing cells and extracting nucleic acids from microorganisms contained in a sample fluid.

2. SUMMARY

The present disclosure relates to improved bead beating tubes and bead beating systems and methods. Without being bound by theory, the inventors believe that bead beating permits nucleic acids to dissolve into solution. The present disclosure is based, in part, on the discovery that the use of bead beating in nucleic acid extraction methods results in nucleic acid loss due to absorption on the beads and that such loss can be prevented by the appropriate amount of blocking agent to block binding sites on the beads. The present disclosure is also based on the recognition that although some lysis buffers previously used in bead beating may contain reagents that act as blocking agents, such reagents may be used in much lower quantity than was typically used. Further, the present disclosure is also based on the recognition that some biological samples, such as blood, inherently contain blocking agents and accordingly may undergo bead beating in the absence of additives such as lysis buffers.

In certain aspects, the disclosure provides bead beating systems that are suitable for use when bead beating samples that do not inherently contain blocking agents or contain blocking agents in amounts below those appropriate for effective blocking of nucleic acid absorption by beads. The bead beating systems of the disclosure include dry blocking agents. Surprisingly, it has turned out that, when using beat beating systems of the disclosure for lysis of microorganisms and extraction of deoxyribonucleic acids (DNA) and/or ribonucleic acids (RNA) from microorganisms contained in a liquid sample, a larger extraction rate of DNA and/or RNA can be achieved than when using a corresponding bead beating tube which does not contain the blocking agent.

The bead beating systems of the disclosure can also circumvent the need to combine a sample with a lysis solution prior to bead beating, allowing the recovery of greater quantities of nucleic acids due to the lack of sample dilution.

In yet other aspects, the disclosure provides methods for performing bead beating to lyse cells and extract nucleic acids from biological samples. The methods comprise performing bead beating on the biological samples in the absence of lysis buffer. The bead beating methods can utilize the bead beating systems of the disclosure or standard bead beating systems. When using standard bead beating systems, in some embodiments one or more blocking agents are added to the bead beating systems. In other embodiments, particularly where a biological sample naturally includes one or more blocking agents, no blocking agent is added prior to bead beating.

In certain embodiments, a bead beating system of the disclosure is composed a sample tube which comprises a container member with an inner cavity, an aperture for filling a sample fluid containing microorganisms into the inner cavity, and an attached or unattached closure for closing the aperture, wherein a plurality of macroscopic particles are arranged in the inner cavity which are adapted to mechanically destroy the cell walls of the microorganisms contained in the sample fluid when the sample fluid is filled into the inner cavity and the bead beating tube is subject to mechanical oscillations. Exemplary bead beading systems are described in Section 4.1 and numbered embodiments 1 to 24 and 67 to 75 below. Exemplary sample tubes that can be used in the bead beating systems are described in Section 4.1.1, exemplary blocking agents that can be used in the bead beating systems are described in Section 4.1.2, and exemplary beads that can be used in the bead beating systems are described in Section 4.1.3.

The disclosure further relates to a method for lysing microorganisms to extract deoxyribonucleic acid (DNA) and/or ribonucleic acid (RNA) from the microorganisms, wherein a sample fluid is provided which is assumed to contain the microorganisms, wherein a plurality of particles movable relative to each other are introduced in the sample fluid and the sample fluid with the particles contained therein is oscillated such that the particles are capable of mechanically destroying cell walls of the microorganisms contained in the sample fluid. Exemplary samples from which DNA can be extracted are described in Section 4.2 and exemplary sample pre-processing steps that can be used to prepare samples prior to nucleic acid extraction are described in Section 4.3. Exemplary methods for extracting nucleic acids from samples, for example from samples described in Section 4.2 or samples that have been pre-processed as described in Section 4.3, are described in Section 4.4 and numbered embodiments 25 to 58 and 76 to 81 below. Kits useful for performing the nucleic acid extraction methods of the disclosure are described in Section 4.7 and numbered embodiments 59 to 66 below.

3. BRIEF DESCRIPTION OF THE FIGURES

FIG. 1: a side view of an exemplary bead beating system (1) comprising a sample tube (2) and a closure cap (6).

Figure 2:
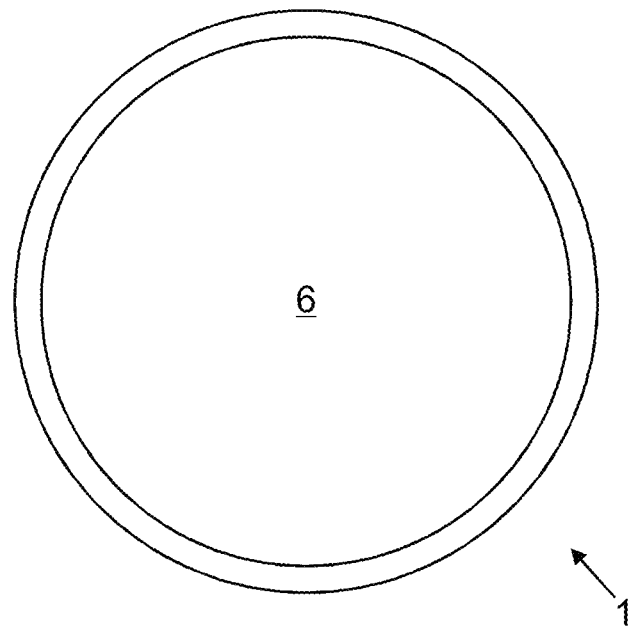

FIG. 2: a plan view of the bead beating system shown in FIG. 1.

Figure 3:
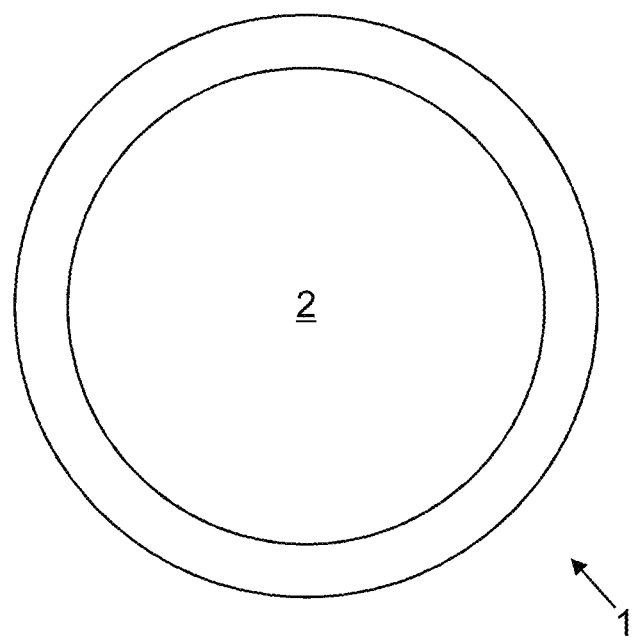

FIG. 3: a bottom view of the bead beating system shown in FIG. 1.

Figure 4:
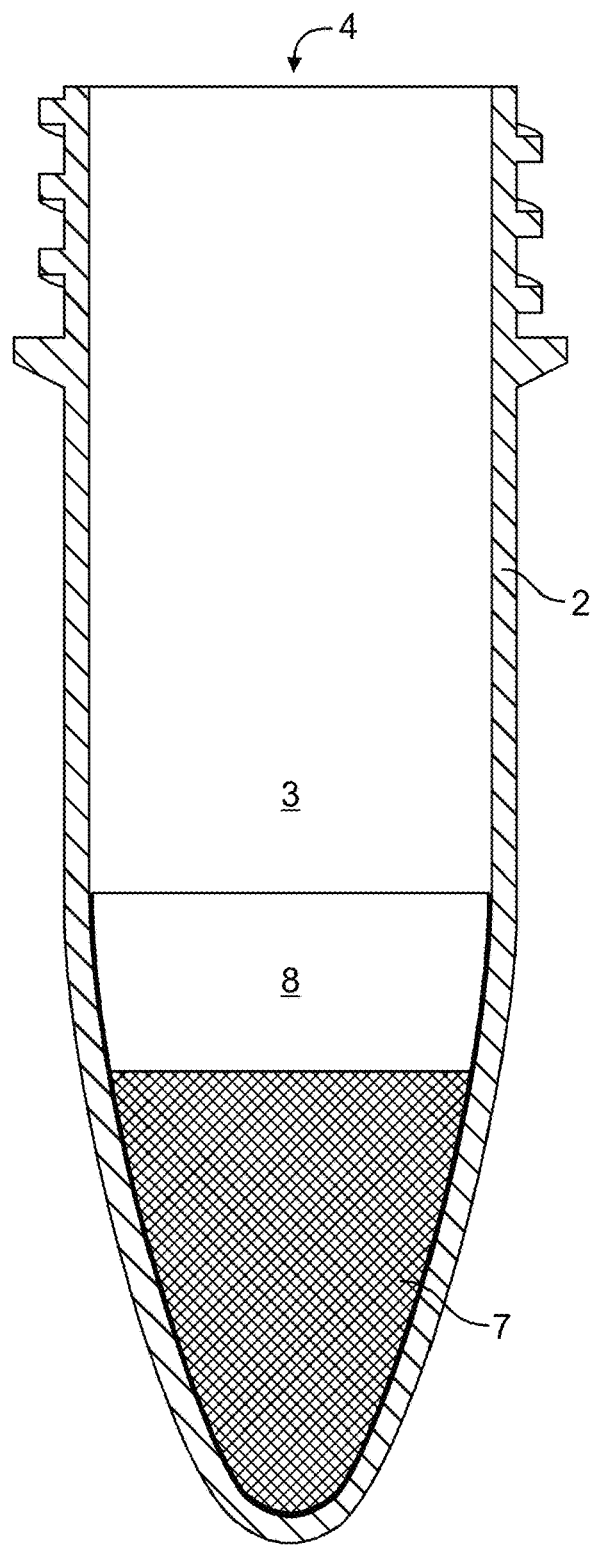

FIG. 4: a longitudinal section through the center plane of the bead beating system shown in FIG. 1 with the closure cap removed from the sample tube, revealing an aperture (4) through which the inner cavity (3) of the sample tube is accessible. Beads (7) and a lyophilized blocking agent (8) are shown in the inner cavity.

Figure 5:
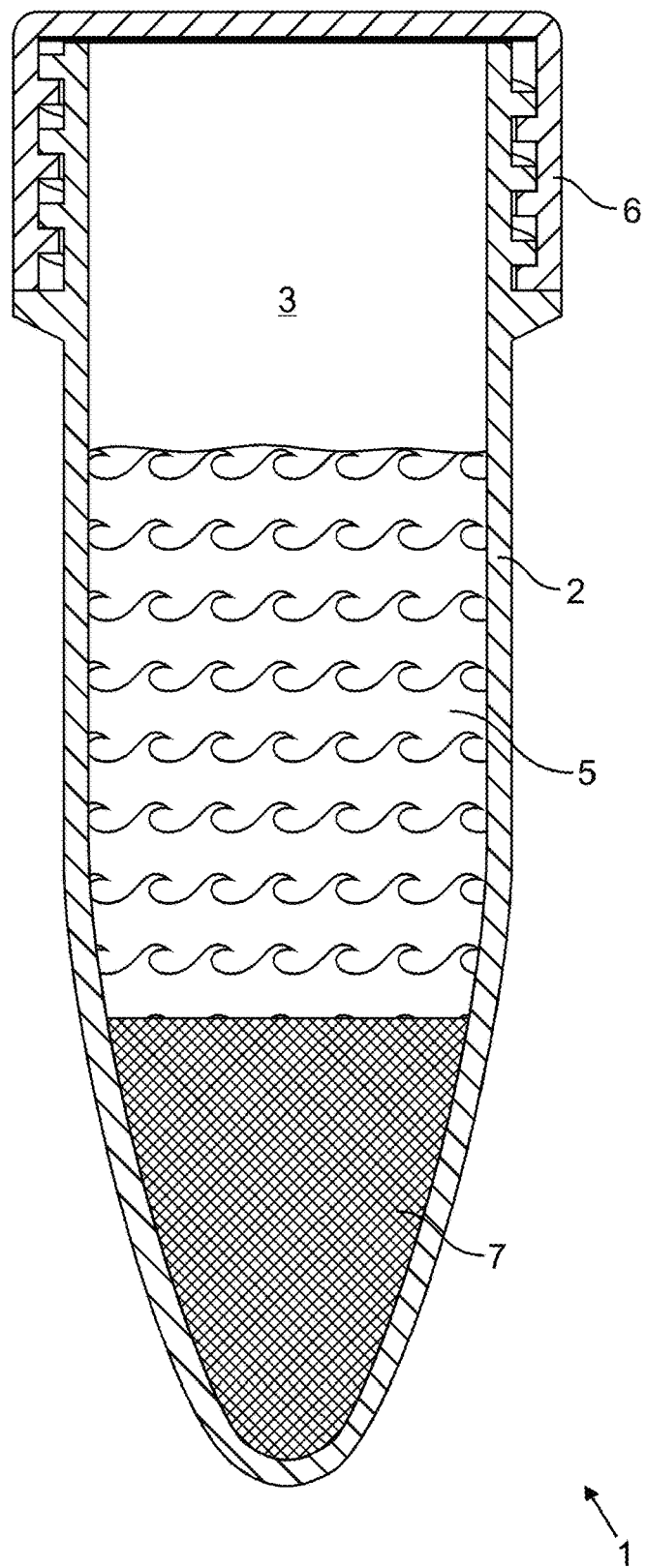

FIG. 5: a longitudinal section through the center plane of a bead beating system shown in FIG. 1 filled with a sample fluid (5).

Figure 6:
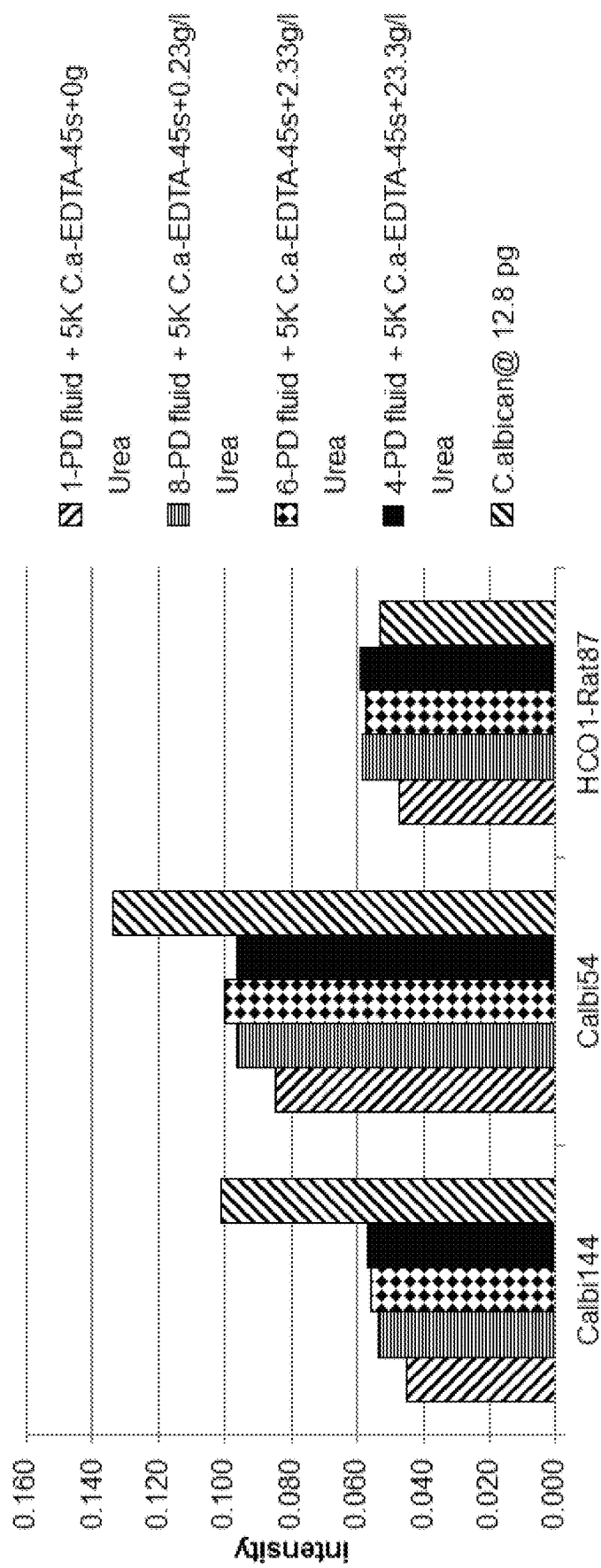

FIG. 6: shows intensity of PCR amplification product using DNA recovered from *C. albicans* after bead beating as a template. Calbi144 and Calbi54 are two different *C. albicans* target genes and HCO1-Rat87 is a negative control gene. This study shows that urea has a blocking effect in bead beating, facilitating the recovery of *C. albicans* DNA from PD fluid.

Figure 7:
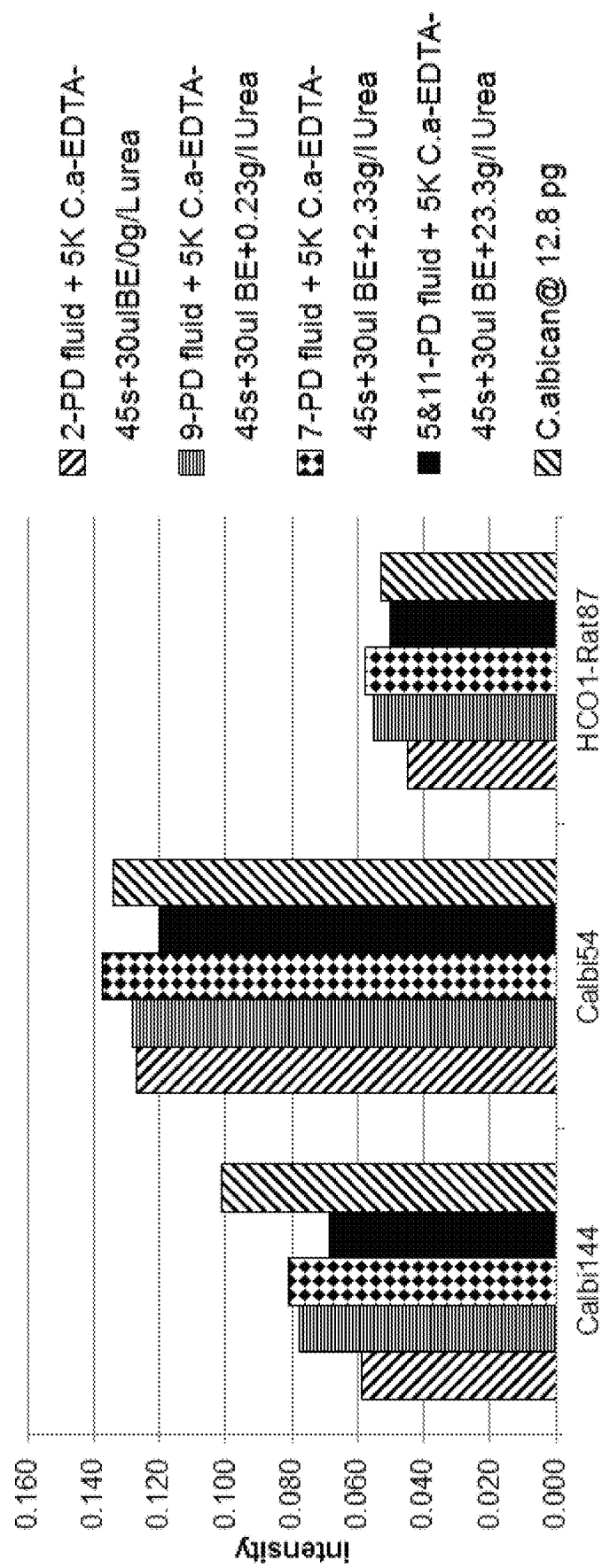

FIG. 7: shows intensity of PCR amplification product using DNA recovered from *C. albicans* after bead beating as a template. Calbi144 and Calbi54 are two different *C. albicans* target genes and HCO1-Rat87 is a negative control gene. This study shows that RNA has a blocking effect in bead beating, facilitating the recovery of *C. albicans* DNA from PD fluid.

Figure 8:
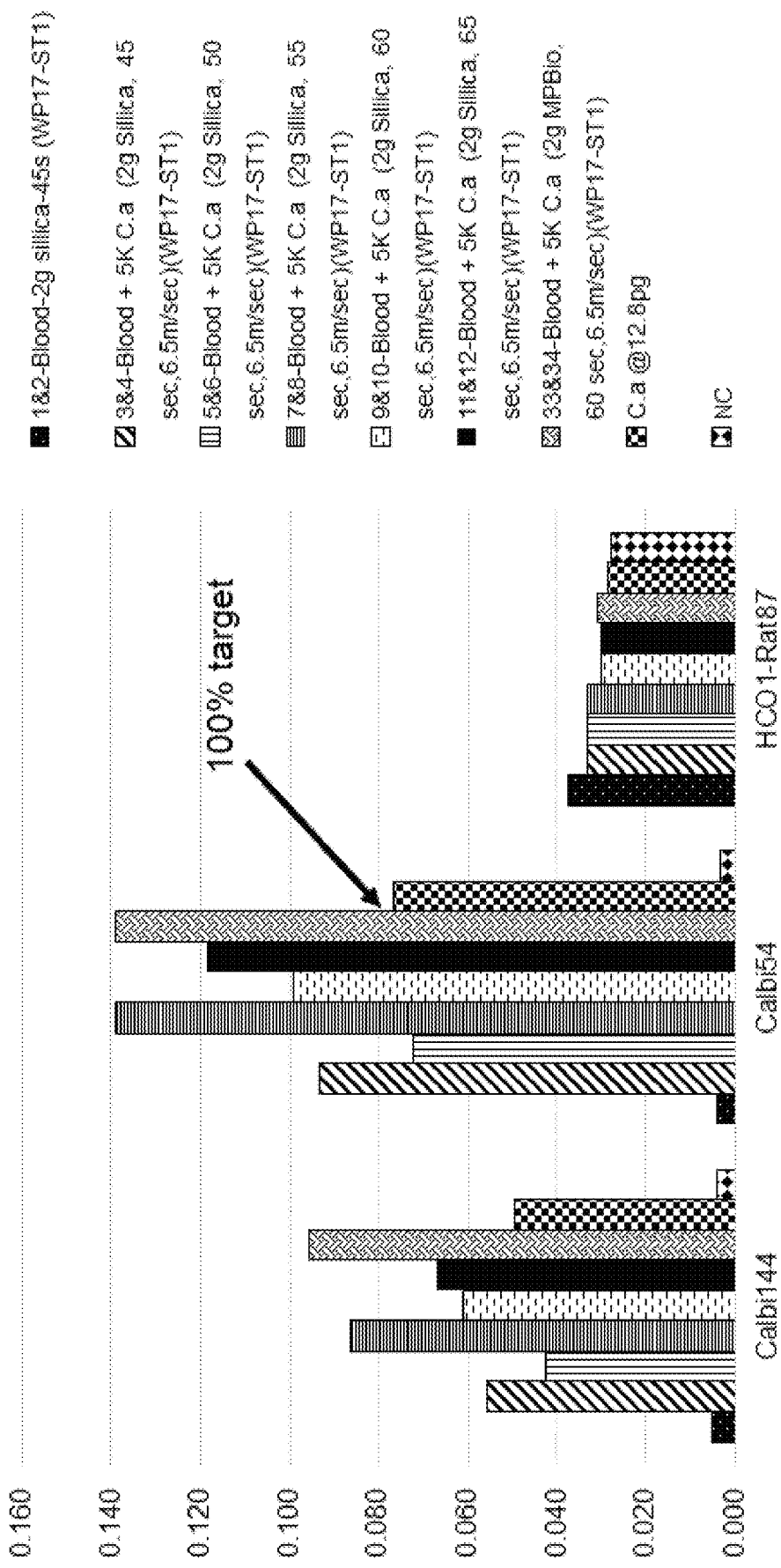

FIG. 8: shows intensity of PCR amplification product using DNA recovered from *C. albicans* after bead beating as a template. Calbi144 and Calbi54 are two different *C. albicans* target genes and HCO1-Rat87 is a negative control gene. An amount of *C. albicans* DNA corresponding to the maximum theoretical yield of extraction was included as a template. This study shows that *C. albicans* DNA can be recovered by bead beating blood in the absence of additives.

Figure 9:
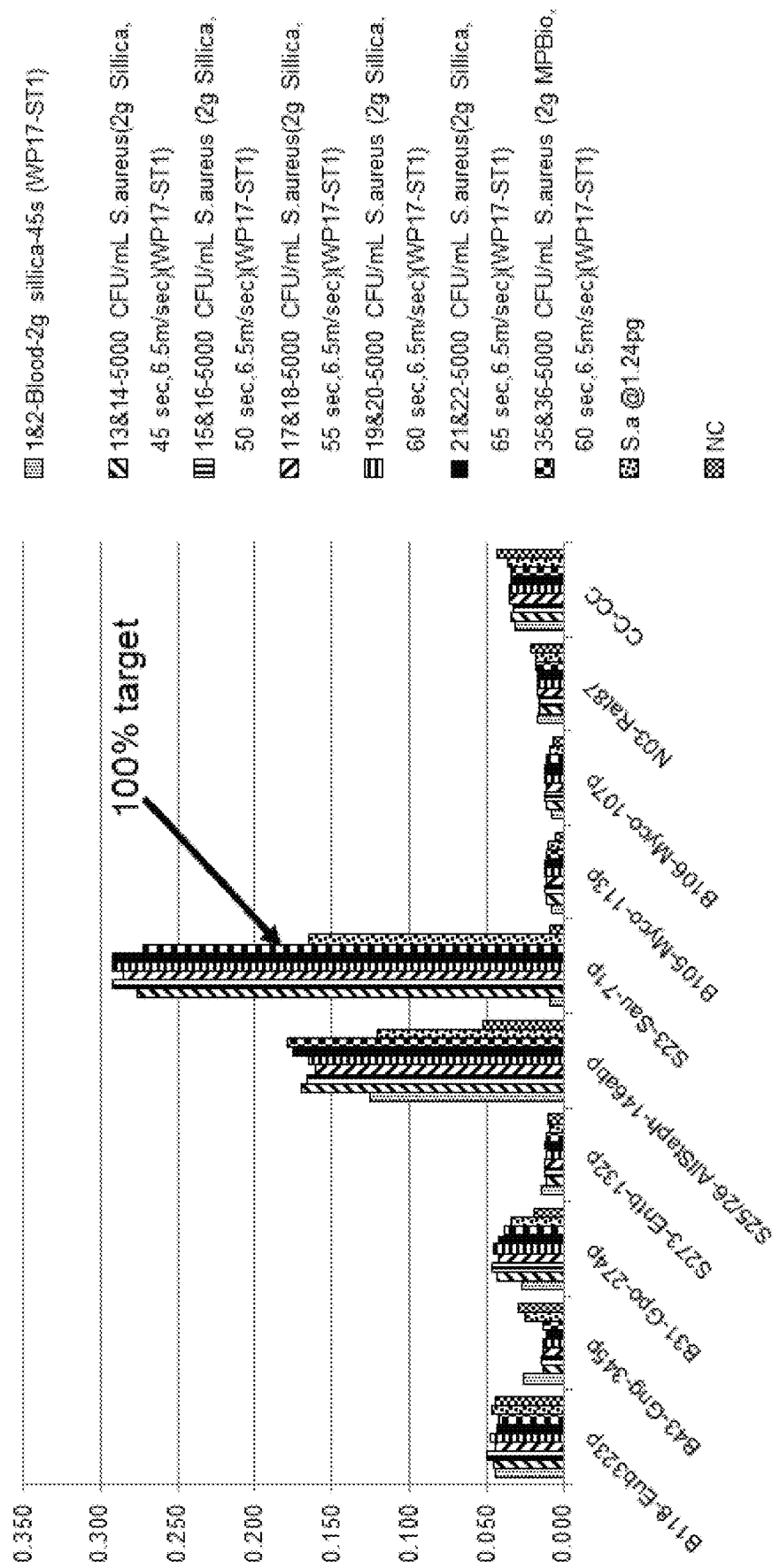

FIG. 9: shows intensity of PCR amplification product using DNA recovered from *C. albicans* after bead beating as a template. The genes probed from are for detection of eubacteria (Eub), gram negative bacteria (Gng), gram positive bacteria (Gpo), *E. coli* (Eco), staphylocci (AllStaph), enterobacteriacae (Ent), *S. aureus* (Sau), mycobacteria (Myco). N03 Rat 87 is a negative control, and CC is an internal control. An amount of *S. aureus* DNA corresponding to the maximum theoretical yield of extraction was included as a template. This study shows that *S. aureus* DNA can be recovered by bead beating blood in the absence of additives.

Figure 10:
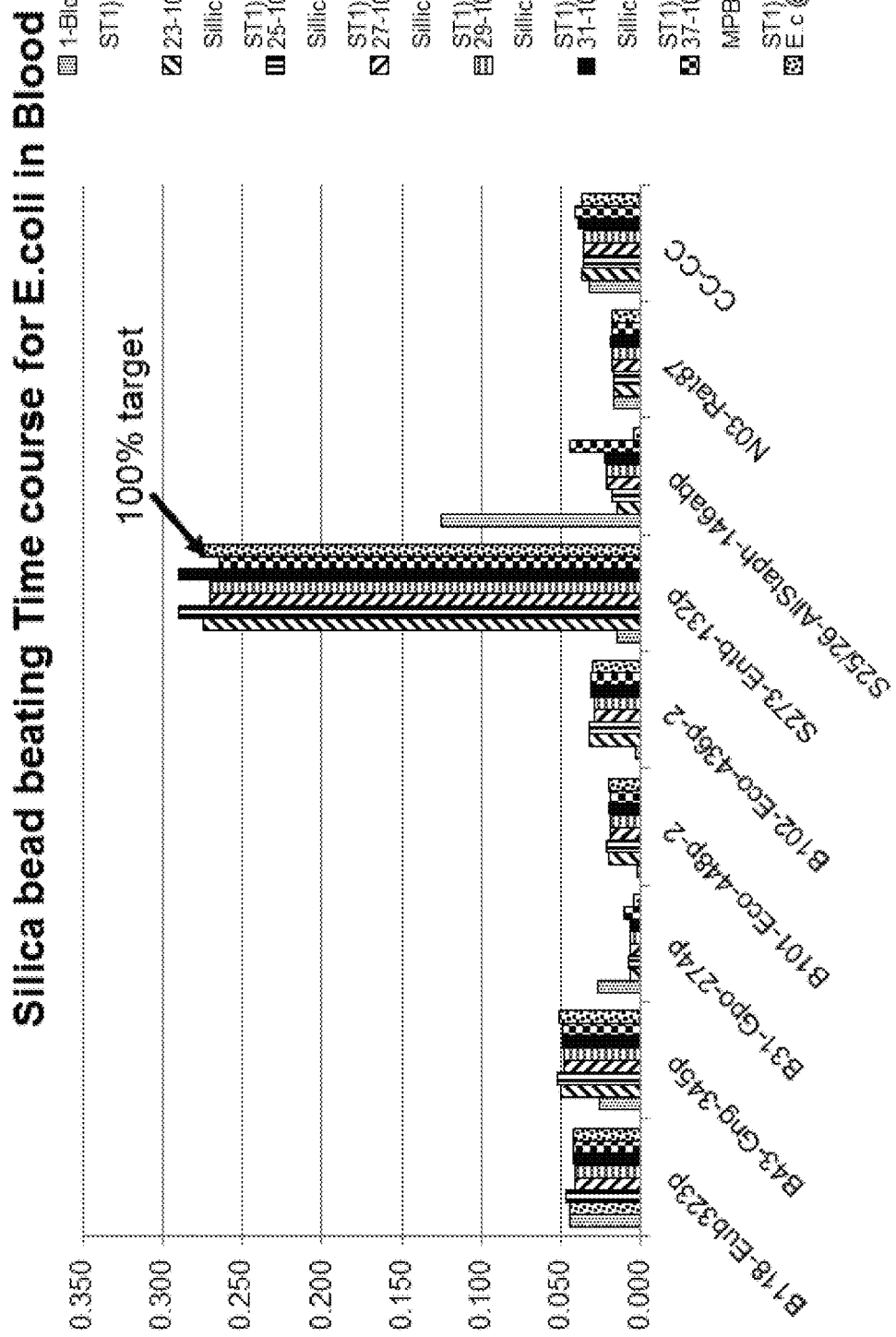

FIG. 10: shows intensity of PCR amplification product using DNA recovered from *C. albicans* after bead beating as a template. The genes probed from are for detection of eubacteria (Eub), gram negative bacteria (Gng), gram positive bacteria (Gpo), *E. coli* (Eco), staphylocci (AllStaph), enterobacteriacae (Ent), *S. aureus* (Sau), mycobacteria (Myco). N03 Rat 87 is a negative control, and CC is an internal control. An amount of *E. coli* DNA corresponding to the maximum theoretical yield of extraction was included as a template. This study shows that *E. coli* DNA can be recovered by bead beating blood in the absence of additives.

4. DETAILED DESCRIPTION

Bead beating is a homogenization process used to lyse cells in order to release their contents, including their nucleic acids (DNA and RNA). Samples are placed in tubes with the appropriate grinding beads and subjected to high energy mixing. The samples are then typically centrifuged and the lysate recovered from above the beads. Typically, samples that are subject to bead beating are treated with lysis buffer to facilitate the release of DNA from cells.

The present disclosure relates to improved bead beating methods and systems. The bead beating methods can be performed without the use of lysis buffer, simplifying the process of cell lysis and nucleic acid extraction and avoiding sample dilution while minimizing loss due to absorption on beads.

The methods of the present disclosure relate to performing bead beating using the appropriate amount of blocking agents. The blocking agents can be exogenous or endogenous to the sample. For example, blood contains urea, a reagent found to block binding of nucleic acids in a biological sample to bead beating beads. Accordingly, the present disclosure provides methods of bead beating such samples without the addition of exogenous blocking agents, although supplementation of endogenous blocking agents with exogenous blocking agents is also contemplated. For biological samples containing no or low amount of endogenous blocking agents, exogenous blocking agents can be used. The present disclosure further provides bead beating systems into which dry blocking agents are incorporated, which allows bead beating biological samples without the addition of reagents that result in sample dilution.

Accordingly, the present disclosure provides bead beating systems that include dry blocking agents. The present disclosure further provides methods for performing bead beating to lyse cells in, and extract nucleic acids from, biological samples. The methods comprise performing bead beating on the biological samples in the absence of lysis buffer. The bead beating methods can utilize the bead beating systems of the disclosure or standard bead beating systems. When using standard bead beating systems, in some embodiments one or more blocking agents are added to the bead beating systems. In other embodiments, particularly where a biological sample naturally includes one or more blocking agents, no blocking agent is added prior to bead beating.

Kits containing (or suitable for obtaining) the bead beating systems of the disclosure are also provided herein.

4.1 Bead Beating System

The present disclosure provides bead beating systems useful for cell lysis and extraction of deoxyribonucleic acids (DNA) and ribonucleic acids (RNA) from cells (e.g., microorganisms) contained in a liquid sample. The bead beating systems of the disclosure comprise a sample tube, and beads and a dry blocking agent situated within the sample tube. Blocking agents that can be used in the bead beating systems of the disclosure include urea, guanidine salts, detergents, nucleotides, and oligonucleotides. Blocking agents are described in detail in Section 4.1.2. Beads that can be used in the bead beating systems of the disclosure include beads comprising a mineral and/or a metal. Beads suitable for use in the bead beating systems of the disclosure are described in Section 4.1.3.

4.1.1 Sample Tube

The bead beating systems of the disclosure comprise a sample tube having an inner cavity that is accessible by an aperture and which can accommodate beads, a blocking agent, and a liquid sample. The sample tube can be made of any biologically inert material (e.g., a plastic or borosilicate), and is preferably made of a plastic (e.g., polypropylene, polypropylene copolymer, or polycarbonate). As used herein, the term "tube" encompasses vials (e.g., grinding vials) and tubes (e.g., conical tubes).

The bead beating system can include a closure for covering the aperture and sealing the sample tube. The closure can be fixed to the sample tube (e.g., a cap fixed to the sample tube by a hinge) or can be separable from the sample tube (i.e., a removable cap). The sample tube can include a threaded region that is adapted to engage a threaded cap. The threads can be on the inner or outer surface of the sample tube (e.g., as shown in FIGS. 4-5).

Sample tubes that can be used in the bead beating system of the disclosure are commercially available, for example, screw-cap polypropylene or microfuge tubes. Standard tube sizes can be used to make the bead beating tubes and systems of the disclosure, for example 0.5 mL, 1.7 mL, 2 mL, 4.5 mL, 7 mL, 15 mL, 50 mL or 250 mL.

4.1.2 Blocking Agent

The bead beating systems of the disclosure include dry blocking agents. As used herein, a "dry" or "dried" blocking agent is a blocking agent that contains less than 20% moisture. In some embodiments, the dry blocking agent contains less than 15%, less than 10%, less than 5%, less than 4%, less than 3%, less than 2%, or less than 1% moisture.

The dry blocking agent is preferably long-term stable, i.e., the bead beating system can be transported and stored without problems for a longer period without the blocking effect of the blocking agent decreasing considerably. The dry blocking agent can be arranged loosely in the inner cavity of the container member, and/or part of or the entire inner cavity of the sample can be coated with a layer or a film of the blocking agent. The blocking agent is preferably lyophilized. The blocking agent can be lyophilized prior or after addition of the beads to the tube.

Examples of blocking agents include one or more chaotropic agents (e.g., urea, guanidine salts), one or more detergents, one or more nucleotides, one or more oligonucleotides, or any combination thereof. Details of such exemplary blocking agents are set forth in Sections 4.1.2.1 to 4.1.2.5, infra. The inclusion of blocking agents that contribute to the lysis of a microbial cell well (e.g., a detergent) may improve the yield of nucleic acids prepared using the bead beating systems of the disclosure and circumvent the need for combining a sample with a lysis solution prior to bead beating. Generally, the quantities of blocking agents used in the bead beating systems of the disclosure are lower than is used in lysis solutions.

A bead beating system can be produced by lyophilizing a lysis solution (also referred to as an extraction buffer or lysis buffer) in a bead beating tube. Lysis solutions containing blocking agents are known in the art or can be purchased commercially.

In some embodiments, the blocking agent comprises one or more chaotropic agents. In some embodiments, the blocking agent comprises one or more detergents. In some embodiments, the blocking agent comprises one or more nucleotides. In some embodiments, the blocking agent comprises one or more oligonucleotides. In some embodiments, the blocking agent comprises one or more chaotropic agents and one or more detergents. In some embodiments, the blocking agent comprises one or more chaotropic agents and one or more nucleotides. In some embodiments, the blocking agent comprises one or more chaotropic agents and one or more oligonucleotides. In some embodiments, the blocking agent comprises one or more detergents and one or more nucleotides. In some embodiments, the blocking agent comprises one or more detergents and one or more oligonucleotides. In some embodiments, the blocking agent comprises one or more nucleotides and one or more oligonucleotides. In some embodiments, the blocking agent comprises one or more chaotropic agents, one or more detergents, and one or more nucleotides. In some embodiments, the blocking agent comprises one or more chaotropic agents, one or more detergents, and one or more oligonucleotides. In some embodiments, the blocking agent comprises one or more chaotropic agents, one or more nucleotides and one or more oligonucleotides. In some embodiments, the blocking agent comprises one or more detergents, one or more nucleotides, and one or more oligonucleotides. In some embodiments, the blocking agent comprises one or more chaotropic agents, one or more detergents, one or more nucleotides, and one or more oligonucleotides.

The blocking agent can further comprise ethylenediaminetetraacetic acid (EDTA) and/or a sodium salt thereof. EDTA binds calcium, magnesium and iron and thus inactivates deoxyribonucleases and ribonucleases. This measure also counteracts degradation of DNA and RNA contained in a sample fluid processed using the bead beating system. Thus, higher detection sensitivity and reproducibility of the measurement results is enabled during an examination of DNA and/or RNA extracted from cells (e.g., microorganisms) using a bead beating system of the disclosure.

The blocking agent can be arranged loosely in the inner cavity of the container member, for example in powdered form. The powder can, for example, be mixed with the beads in the sample, or can be arranged in the sample tube as a layer above and/or below the beads. Alternatively or additionally, the inner wall of the sample tube can be at least partially coated with a layer or a film of the blocking agent. The layer or film can be prepared by evaporating the liquid from an aqueous mixture comprising the blocking agent that has been added to the sample tube. In another embodiment, some or all of the beads in the bead beating system can be coated with the blocking agent.

4.1.2.1 Chaotropic Agents

Chaotropic agents disrupt the structure of, and denature, macromolecules such as proteins and nucleic acids. Chaotropic solutes decrease the net hydrophobic effect of hydrophobic regions because of a disordering of water molecules adjacent to the protein. This solubilizes the hydrophobic region in the solution, thereby denaturing the protein. This is also directly applicable to the hydrophobic region in lipid bilayers; if a critical concentration of a chaotropic solute is reached (in the hydrophobic region of the bilayer) then membrane integrity will be compromised, and the cell will lyse.

Exemplary chaotropic agents that can be used as blocking agents are provided below.

Urea: When the blocking agent comprises urea (or thiourea; as used herein, unless the context dictates otherwise, the term urea includes thiourea), the amount of urea can be aligned with the amount of the sample fluid that is intended to be used with the bead beating system such that the concentration of the urea dissolved in the sample fluid after addition of the sample fluid to the sample tube ranges between 10 and 100 grams per liter, between 50 and 100 grams per liter, between 20 and 50 grams per liter, or between 25 and 35 grams per liter. Thus, with respect to the foregoing embodiments, in case of a 2 mL tube to which 1 mL of sample is to be added, the amount of urea used in the blocking reagent will be between 10 and 100 mg, between 50 and 100 mg, between 20 and 50 mg, or between 25 and 35 mg, respectively, and in case of a 2 mL tube to which 0.8 mL of sample is to be added, the amount of urea used in the blocking reagent will be between 8 and 80 mg, between 40 and 80 mg, between 16 and 40 mg, or between 20 and 28 mg, respectively.

Salts: Certain salts can behave as chaotropic agents. Salts can have chaotropic properties by shielding charges and preventing the stabilization of salt bridges. Chaotropic salts include various salts of guanidine, lithium and magnesium.

Guanidine Salts: Guanidine salts that can be used as blocking agents in the bead beating systems of the disclosure include guanidine isocyanate, guanidine chloride, and combinations thereof.

Lithium Salts: Lithium salts that can be used as blocking agents in the bead beating systems of the disclosure include lithium perchlorate, lithium acetate, and combinations thereof.

Magnesium Salts: Magnesium salts that can be used as blocking agents in the bead beating systems of the disclosure include magnesium chloride.

Detergents: Certain detergents can act as chaotropic agents, for example sodium dodecyl sulfate ("SDS"). The use of detergents as blocking agents is described in Section 4.1.2.3.

4.1.2.2 Creatinine

When the blocking agent comprises creatinine, the presence of the creatinine in the inner cavity of the sample tube can counteract degradation of DNA and/or RNA contained in a sample processed using the bead beating system. Furthermore, creatinine prevents the DNA and/or the RNA from nonspecifically binding to the beads and/or the inner wall of the sample tube. This enables larger yield when extracting DNA and/or RNA from cells (e.g., microorganisms) processed using the bead beating tube system.

4.1.2.3 Detergents

Detergents that can be used as blocking agents in the bead beating systems of the disclosure include sodium dodecyl sulfate, sodium lauroylsulfate sarcosinate, polyoxyethylene (20) sorbitan monolaurate, and combinations thereof. Polyoxyethylene (20) sorbitan monolaurate is also known as polysorbate 20.

The amount of the detergent used in the blocking agent can be aligned with the amount of the sample fluid that is intended to be used with the bead beating system. In certain embodiments, the concentration of detergent dissolved in the sample fluid after addition of the sample fluid to the sample tube ranges from 1 to 50 mg/mL, from 1 to 25 mg/mL, or from 25 to 50 mg/mL. Thus, with respect to the foregoing embodiments, in case of a 2 mL tube to which 1 mL of sample is to be added, the amount of detergent used in the blocking agent will range 1 to 50 mg, from 1 to 25 mg, or from 25 to 50 mg, respectively, and in case of a 2 mL tube to which 0.8 mL of sample is to be added, the amount of detergent used in the blocking agent will range from 0.8 to 40 mg, from 0.8 to 20 mg, or from 20 to 40 mg.

4.1.2.4 Nucleotides

Nucleotides that can be used in the bead beating systems of the disclosure include ribonucleotides, deoxyribonucleotides, and combinations thereof.

The nucleotides can be naturally occurring. Naturally occurring ribonucleotides are adenosine monophosphate, guanosine monophosphate, cytosine monophosphate, and thymidine monophosphate. Naturally occurring deoxyribonucleotides that can be used are blocking agents are deoxyadenosine monophosphate, deoxyguanosine monophosphate, deoxycytosine monophosphate, and deoxythymidine monophosphate.

The nucleotides can be non-naturally occurring analogs of naturally occurring nucleotides. Examples of non-naturally occurring analogs include, but are not limited to, peptide nucleotides, locked nucleic acid ("LNA") nucleotides (which contain bicyclic sugar moieties instead of a deoxyribose or ribose sugars), those with uncharged linkages (e.g., methyl phosphonates, phosphotriesters, phosphoroamidates, carbamates, etc.) and with charged linkages (e.g., phosphorothioates, phosphorodithioates, etc.), and those containing pendant moieties. In specific embodiments, the analog is 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxy-aminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine, or 7-deazaguanosine.

In some embodiments, the blocking agent comprises a mixture of at least two, at least three, or four naturally occurring ribonucleotides. In other embodiments, the blocking agent comprises a mixture of at least two, at least three, or four naturally occurring deoxyribonucleotides. In yet other embodiments, the blocking agent comprises a mixture of at least two, at least three, four or even more than four nucleotide analogs. In yet other embodiments, the blocking agent comprises a mixture of (a) naturally occurring ribonucleotides and naturally occurring deoxyribonucleotides, (b) naturally occurring ribonucleotides and nucleotide analogs (c) naturally occurring deoxyribonucleotides and nucleotide analogs; or (d) naturally occurring ribonucleotides, naturally occurring deoxyribonucleotides and nucleotide analogs.

The amount of the ribonucleotides used in the blocking agent can be aligned with the amount of the sample fluid that is intended to be used with the bead beating system. In certain embodiments, the concentration of ribonucleotides dissolved in the sample fluid after addition of the sample fluid to the sample tube ranges from 200 pg/ml to 20 µg/mL, from 1 ng/ml to 15 µg/ml, or from 1 µg/ml to 10 µg/ml. Thus, with respect to the foregoing embodiments, in case of a 2 mL tube to which 1 mL of sample is to be added, the amount of ribonucleotides used in the blocking agent will range from 200 pg to 20 µg, from 1 ng to 15 µg, or from 1 µg to 10 µg, respectively, and in the case of a 2 mL tube to which 0.8 mL of sample is to be added, the amount of ribonucleotides used in the blocking agent will range from 160 pg to 16 µg, from 0.8 ng to 12 µg, or from 0.8 µg to 8 µg.

4.1.2.5 Oligonucleotides

Oligonucleotides useful as blocking agents can be synthesized or generated from naturally occurring sources.

"Oligonucleotide" as referred herein does not connote the size of the molecule and means a polymeric form of nucleotides of any length. However, typically oligomers are no greater than 2,000 nucleotides, 1,000 nucleotides, more typically are no greater than 500 nucleotides, and even more typically are no greater than 250 nucleotides. The term oligonucleotide includes double- and single-stranded DNA and RNA (but is preferably at least partially single-stranded). It also includes known types of modifications, for examples, labels which are known in the art, methylation, "caps", substitution of one or more of the naturally occurring nucleotides with an analog (such as those described in Section 4.1.2.4), such as, for example.

The oligonucleotides can be a mixture of different sizes and/or can comprise ribonucleotides, deoxyribonucleotides, nucleotide analogs or a combination of two or more of the foregoing (e.g., a mixture of ribonucleotides and deoxyribonucleotides, a mixture of ribonucleotides and nucleotide analogs, a mixture of deoxyribonucleotides and nucleotide analogs, or a mixture of ribonucleotides, deoxyribonucleotides, and nucleotide analogs). In some embodiments, the blocking agent comprises RNA.

Synthetic oligonucleotides that can be used in the bead beating systems of the disclosure are typically 2 to 120 nucleotides long. In various embodiments, the oligonucleotides are 2, 5, 8, 10, 15, 18, 25, 40, 50, 80, 100 or 120 nucleotides long, or oligonucleotides having a length ranging between any pair of the foregoing values, e.g., 2 to 100 nucleotides long, 2 to 50 nucleotides long, 2 to 25 nucleotides long, 5 to 40 nucleotides long, 2 to 15 nucleotides long, 8 to 120 nucleotides long, 8 to 80 nucleotides long, 10 to 100 nucleotides long, 15 to 50 nucleotides long, 50 to 100 nucleotides long, 100 to 120 nucleotides long, and so on and so forth.

Naturally occurring oligonucleotides can prepared by shearing DNA from one or more naturally occurring sources, e.g., salmon sperm DNA, calf thymus DNA, herring sperm DNA, or combinations thereof.

The amount of the oligonucleotides used in the blocking agent can be aligned with the amount of the sample fluid that is intended to be used with the bead beating system. In certain embodiments, the concentration of oligonucleotides dissolved in the sample fluid after addition of the sample fluid to the sample tube ranges from 200 pg/ml to 20 µg/mL, from 1 ng/ml to 15 µg/ml, or from 1 µg/ml to 10 µg/ml. Thus, with respect to the foregoing embodiments, in case of a 2 mL tube to which 1 mL of sample is to be added, the amount of oligonucleotides used in the blocking agent will range from 200 pg to 20 µg, from 1 ng to 15 µg, or from 1 µg to 10 µg, respectively, and in the case of a 2 mL tube to which 0.8 mL of sample is to be added, the amount of ribonucleotides used in the blocking agent will range from 160 pg to 16 µg, from 0.8 ng to 12 µg, or from 0.8 µg to 8 µg.

4.1.3 Beads

The bead beating system of the disclosure comprises beads that are movable relative to each other when they are arranged in the sample fluid. As used herein, the term "bead" encompasses both spherical and non-spherical particles. The beads can be mineral beads, for example those made of crystalline particles (e.g., zirconium, zircon (zirconium silicate) and zirconia (zirconium dioxide), quartz, aluminum oxide, silicon carbide (also known as carborundum), ceramic particles, glasses (e.g., silicon dioxide glass or silica), or combinations comprising one or more of the foregoing (e.g., zirconia/silica beads or zirconia/yttrium beads). The beads can also be metal beads, for example stainless steel beads or chrome-steel beads.

For recovery of bacterial DNA, the beads preferably include quartz particles and/or zirconium particles. Such beads are commercially available in large amounts and are chemically inert with respect to DNA and RNA. Quartz and/or zirconium particles have a relatively high specific weight, are hard and may have sharp edges. Therefore, they are well suited for opening cell membranes when exposed to mechanical vibrations.

The material and size of the beads for a given bead beating system can be selected by those skilled in the art based upon the identity of the cell types in a fluid sample to be processed. Generally, the beads will range from 50 µm to 3 mm in diameter. For extracting nucleic acids from bacterial cells, small to medium sized beads, typically made of glass or zirconium and ranging from 50 µm to 0.5 mm in diameter, can be used. For extracting nucleic acids from larger microbial cells such as yeast, medium sized or large beads (e.g., beads with diameters of 0.5 mm, 1 mm or 1.5 mm beads, typically made of glass or zirconium) can be used. Beads of different sizes and compositions for processing different cell types are commercially available. See, e.g., Benchmark Scientific, Product Note: Benchmark Bead Beating Guide, available at www.denvillescientific.com/sites/default/files/Bead_Blasting_Notes.pdf.

The bead beating systems of the disclosure can include multiple types of beads and/or multiple sizes of beads of the same type, particularly where recovery of nucleic acid from multiple sources is desired (e.g., bacterial and fungal DNA). Examples of bead beating systems with multiple types of beads include systems with a combination of aluminum oxide beads and silicon carbide beads, a combination of ceramic beads and silica beads, a combination of glass beads and zirconium oxide beads, a combination of zirconia beads and aluminum oxide beads, or a combination of silicon carbide beads and glass beads. The different types of beads can be the same or different sizes.

4.2 Samples

Examples of samples from which nucleic acids may be extracted using the bead beating methods of the disclosure include various fluid samples. In some instances, the sample may be a bodily fluid sample from the subject. The sample may include tissue collected from the subject. The sample may include a bodily fluid, secretion, and/or tissue of a subject. The sample may be a biological sample. The biological sample may be a bodily fluid, a secretion, and/or a tissue sample. Examples of biological samples may include but are not limited to, blood, serum, saliva, urine, gastric and digestive fluid, tears, stool, semen, vaginal fluid, interstitial fluids derived from tumorous tissue, ocular fluids, sweat, mucus, earwax, oil, glandular secretions, breath, spinal fluid, hair, fingernails, skin cells, plasma, nasal swab or nasopharyngeal wash, spinal fluid, cerebrospinal fluid, tissue, throat swab, wound swab, biopsy, placental fluid, amniotic fluid, cord blood, emphatic fluids, cavity fluids, sputum, pus or other wound exudate, infected tissue sampled by wound debridement or excision, cerebrospinal fluid, lavage, leucopoiesis specimens, peritoneal dialysis fluid, milk and/or other excretions.

The sample may be placed into a bead beating tube fresh from a subject or may have undergone some form of pre-processing (for example as described in Section 4.3 below), storage, or transport prior to placement in a bead beating tube. The sample may be added to a bead beating system without undergoing intervention or much time.

A subject may provide a sample, and/or the sample may be collected from a subject. The subject can be a human or a non-human animal. The sample may be collected from a living or dead subject. The animal can be a mammal, such as a farm animal (e.g., cow, pig, sheep), a sport animal (e.g., horse), or a pet (e.g., dog or cat). The subject may be a patient, clinical subject, or pre-clinical subject. A subject may be undergoing diagnosis, treatment, and/or disease management or lifestyle or preventative care. The subject may or may not be under the care of a health care professional.

In some embodiments, the sample may be an environmental sample. Examples of environmental samples may include air samples, water samples (e.g., groundwater, surface water, or wastewater), soil samples, or plant samples.

Additional samples may include food products, beverages, manufacturing materials, textiles, chemicals, therapies, or any other samples.

4.3 Sample Pre-Processing

In some instances, it might be advantageous to pre-process a sample prior to processing in a bead beating system of the disclosure. Examples of pre-processing steps that can be used prior to placing a sample in a bead beating tube include filtration, distillation, extraction, concentration, centrifugation, inactivation of interfering components, addition of reagents, and the like, as discussed herein or otherwise as is known in the art.

It would be particularly advantageous to remove unwanted cell types and particulate matter from biological samples prior to their placement into a bead beating tube of the disclosure to maximize recovery of DNA from a cell type of interest.

If the intent is to detect bacteria in a biological sample, then it is desirable to pre-process the biological sample through a filter so that particulates and non-bacterial cells are retained on a filter while bacterial cells (including their spores, if desired) pass through. A "filter," as used herein, is a membrane or device that allows differential passage of particles and molecules based on size. Typically this is accomplished by having pores in the filter of a particular nominal size. For instance, filters of particular interest for bacterial detection applications have pores sufficiently large to allow passage of bacteria but small enough to prevent passage of eukaryotic cells that present in a sample of interest. Generally, bacterial cells range from 0.2 to 2 µm (micrometers or microns) in diameter, most fungal cells range from 1 to 10 µm in diameter, platelets are approximately 3 µm diameter and most nucleated mammalian cells are typically 10 to 200 µm in diameter. Therefore, filter pore sizes of less than 2 µm or less than 1 µm are particularly suitable for removing non-bacterial cells from a biological sample if detection of bacteria is intended.

In addition to or in lieu of a filtration step, a biological sample can be subject to centrifugation to remove cells and debris from a sample prior to bead beating. Centrifugation parameters that precipitate eukaryotic but not bacterial cells are known in the art. The supernatant can then be filtered if desired.

The filtrate generated by a filtration step can be the "sample" and placed into a bead beating tube according to the disclosure, or subject to further pre-processing steps (e.g., concentration or dilution).

4.4 Bead Beating

As an initial step in nucleic acid preparation, a sample is placed into a bead beating tube for bead beating. The bead beating step can utilize a bead beating system of the disclosure or a standard bead beating system. In some instances, one or more exogenous blocking agents can be added when using a standard bead beating system but, in the case of biological samples containing endogenous blocking agents, the addition of exogenous blocking agents is not necessary. When one or more blocking agents are added, they can be added to a bead beating tube prior to addition of the sample, after the addition of the sample, or both the sample and the blocking agent(s) can be added simultaneously (for example, the sample and the blocking agent(s) can be mixed and then transferred to a bead beating tube).

After placing the sample in the bead beating tube, the tube is subject to agitation to mechanically lyse the cells. Lysis can be achieved by a common laboratory vortexer or a homogenizer. While processing time in a vortexer is 3-10 times longer than that in a specialty homogenizer, vortexing works for easily disrupted cells and is inexpensive.

Many homogenizers suitable for bead beating are commercially available and can be used with the beat beating systems of the disclosure. Exemplary homogenizers are the Bead Bug and BeadBlaster 24 (Benchmark Scientific), PowerLyzer 24 (MO Bio Laboratories Inc.), FastPrep-24, FastPrep-24 5G and SuperFastPrep-1 (MP Biomedicals), and Mini-Bead beater-16 (BioSpec Products).

The homogenization parameters can be chosen according to the manufacturer's recommendations. Generally, the duration of mechanical disruption (e.g., bead beating) can be less than 1 sec, 1-5 sec, 5-10 sec, 10-25 sec, 25-60 sec, 1 min-2 min, 2 min-5 min, 5 min or longer. The number of repetitions of mechanical disruption (e.g., number of bead beating sessions) can be 2, 3, 4, 5, 6, 7, 7-10, 10 or more repetitions. The speed of disruption (e.g., speed or setting for bead beating) may be less than 50, 50-100, 100-250, 250-500, 500-750, 750-1000, 1000-1500, 1500-2000, 2000 or more rotations (oscillations) per minute.

4.5 Nucleic Acid Purification

After cell lysis, the fluid sample is separated from the beads, for instance by removing the liquid sample from the sample tube by means of a pipette or the like, leaving behind the beads, which deposit on the bottom of the sample tube.

Impurities that might interfere with analysis of the extracted DNA can be removed, for example by precipitation of the impurities by known methods such as with ammonium acetate or using a commercial kit.

The nucleic acid can be recovered and washed and optionally further purified. Recovery and/or purification of nucleic acid can be carried out using routine methods such as by precipitation with isopropanol or using a commercial kit or an automated instrument.

4.6 Nucleic Acid Analysis

The analysis of a sample for the presence of nucleic acids of interest (such as bacterial or fungal DNA) can be performed using any nucleic acid analysis method including, but not limited to amplification technologies, polymerase chain reaction (PCR), isothermal amplification, reverse transcription polymerase chain reaction (RT-PCR), quantitative real time polymerase chain reaction (Q-PCR), digital PCR, gel electrophoresis, capillary electrophoresis, mass spectrometry, fluorescence detection, ultraviolet spectrometry, hybridization assays, DNA or RNA sequencing, restriction analysis, reverse transcription, NASBA, allele specific polymerase chain reaction, polymerase cycling assembly (PCA), asymmetric polymerase chain reaction, linear after the exponential polymerase chain reaction (LATE-PCR), helicase-dependent amplification (HDA), hot-start polymerase chain reaction, intersequence-specific polymerase chain reaction (ISSR), inverse polymerase chain reaction, ligation mediated polymerase chain reaction, methylation specific polymerase chain reaction (MSP), multiplex polymerase chain reaction, nested polymerase chain reaction, solid phase polymerase chain reaction, or any combination thereof. Such technologies are well known to those skilled in the art. Knowing the sequence of a target nucleic acid enables the scientist to construct primers and/or probes that allow amplification and/or detection of the target. PCR amplicons can also be sequenced to confirm their identity.

By means of the bead beating system in accordance with the disclosure it is possible to extract DNA and/or RNA from the microorganisms contained in the sample fluid in a concentration sufficient to directly examine the DNA and/or RNA microbiologically with per se known methods. This may in particular occur by contacting the sample fluid with receptors immobilized on a surface, which bind specifically to the DNA and/or RNA and/or to DNA and/or RNA components contained therein. The binding of the DNA and/or RNA and/or of the DNA and/or RNA components to the receptors may be detected in a per se known manner by means of markers, in particular optical markers such as fluorescent dyes, and be quantified if necessary. Alternatively, DNA and/or RNA from the microorganisms contained in the sample fluid can be amplified prior to examination, for example, by PCR.

4.7 Kits

The present disclosure further provides kits containing (or suitable for obtaining) the bead beating systems of the disclosure. The kits can comprise a sample tube, such as a sample tube described in Section 4.1.1, one or more or blocking agents, such as those described in Section 4.1.2, and/or one or more types of beads, such as those described in Section 4.1.3. Each of the one or more blocking agents can be pre-lyophilized and can be included within the tube or separately from the tube. Likewise, the beads can be included within the tube or separately from the tube.

In some embodiments, the kit comprises a sample tube and one or more blocking agents. In a further embodiment, the kit further comprises one or more types of beads.

The kits of the disclosure can include one or more components for sample pre-processing, e.g., saline, one or more buffer solutions, a filter as described in Section 4.3, etc.

The kits can include one or more oligonucleotides for amplifying DNA and/or RNA from one or more pathogens of interest (e.g., one or more of *Mycobacterium tuberculosis, Mycobacterium avium* subsp paratuberculosis, *Staphylococcus aureus*, methicillin resistant *Staphylococcus aureus* (MRSA), *Streptococcus pyogenes, Streptococcus pneumoniae, Streptococcus agalactiae, Haemophilus influenzae, Haemophilus parainfuluezae, Moraxella catarrhalis, Klebsiella pneumoniae, Escherichia coli, Pseudomonas aeruginosa, Acinetobacter* sp., *Bordetella pertussis, Neisseria meningitidis, Bacillus anthracis, Nocardia* sp., *Actinomyces* sp., *Mycoplasma pneumoniae, Chlamydia pneumonia, Legionella* species, *Pneumocystis jiroveci*, influenza A virus, cytomegalovirus, rhinovirus, *Enterococcus faecium, Acinetobacter baumannii, Corynebacterium amycolatum, Enterobacter aerogenes, Enterococcus faecalis* CI 4413, *Serratia marcescens, Streptococcus equi*, and *Candida albicans*).

The kits can include one or more probes for detecting DNA and/or RNA from one or more pathogens of interest (e.g., one or more of *Mycobacterium tuberculosis, Mycobacterium avium* subsp paratuberculosis, *Staphylococcus aureus*, methicillin resistant *Staphylococcus aureus* (MRSA), *Streptococcus pyogenes, Streptococcus pneumoniae, Streptococcus agalactiae, Haemophilus influenzae, Haemophilus parainfuluezae, Moraxella catarrhalis, Klebsiella pneumoniae, Escherichia coli, Pseudomonas aeruginosa, Acinetobacter* sp., *Bordetella pertussis, Neisseria meningitidis, Bacillus anthracis, Nocardia* sp., *Actinomyces* sp., *Mycoplasma pneumoniae, Chlamydia pneumonia, Legionella* species, *Pneumocystis jiroveci*, influenza A virus, cytomegalovirus, rhinovirus, *Enterococcus faecium, Acinetobacter baumannii, Corynebacterium amycolatum, Enterobacter aerogenes, Enterococcus faecalis* CI 4413, *Serratia marcescens, Streptococcus equi*, and *Candida albicans*). In an embodiment, the one or more probes comprise oligonucleotides labeled with a fluorescent dye. Different probes can be labeled with different dyes to enable simultaneous detection of multiple pathogens of interest.

5. EXEMPLARY BEAD BEATING SYSTEM

An exemplary bead beating system is shown in the Figures. A bead beating system designated with reference character (1) in FIGS. 1 to 3 comprises a sample tube (2) having an inner cavity (3) and a closable aperture (4). The sample tube is preferably made of a plastic, but may also be made of another biologically inert material.

A sample fluid (5), which is assumed to contain microorganisms, may be filled into the inner cavity (3) of the sample tube (2) and removed therefrom through the aperture (4). For closing the aperture (4) the sample tube has a closure (6) adapted to be conveyed to an open and a closed position and being designed as a closure cap comprising an inner thread which is adapted to be screwed with an outer thread provided on the edge region of the outer wall of the sample tube (2) which bounds the aperture (4).

In the inner cavity (3), beads (7) (e.g., 2 grams of silicon dioxide and/or zirconium beads) are further arranged whose largest dimension is approximately 100 µm on average. The beads (7) are available in the form of a loose bulk in which they are movable relative to each other. A lyophilized blocking agent (8) is also arranged in the inner cavity (3).

The beads (7) serve to mechanically destroy the cell walls of the microorganisms contained in the sample fluid (5) when the sample fluid (5) is filled into the inner cavity (3) and the bead beating tube is subject to mechanical oscillations, for instance, ultrasonic oscillations. They may be generated with an oscillation generator which is not illustrated in detail in the drawing and may be transferred to the bead beating system (1). Such oscillation generator is commercially available under the designation MPBio bead beater from MP Biomedicals. Due to the destruction of the cell walls the nucleic acids (e.g., DNA) contained in the microorganisms are released and dissolved in the sample fluid (5).

6. CASE STUDIES

6.1 Use of Bead-Beating to Recover Pathogen DNA from Sputum

*Mycobacterium tuberculosis* ("MTB") is an obligate pathogenic bacterial species in the family Mycobacteriaceae and the causative agent of most cases of tuberculosis. Primarily a pathogen of the mammalian respiratory system, it infects the lungs. Evidence suggests mycobacteria are able to enter into a state of non-replication or dormancy (spore formation) during stress like nutrient deficiency or hypoxia. The formation of spores makes it challenging to lyse bacterial cells to extract bacterial DNA.

Further complicating recovering of mycobacterial DNA is that *mycobacterium* strains are typically isolated from sputum of infected patients. Sputum is thick, viscous and difficult to process. Most sputum specimens for analysis contain various amounts of organic debris and a variety of contaminating, normal, or transient bacterial flora. Chemical decontamination/processing is typically used to reduce the viscosity and kill the contaminants while allowing recovery of the mycobacteria.

Samples suspected of containing MTB present a potential risk to the user. Accordingly, a sputum sample may be pre-treated by heating and/or inclusion of reagents suitable for inactivating microbes present in the sample to mitigate this risk. Inactivation of microbes, such as MTB, may be carried out by heating (e.g., 90° C., 5 min.) to denature active proteins, enzymatic digestion of cell wall structures, mechanical disruption to physically disrupt or inactivate the cells, chemical treatment or a combination thereof.

A sputum sample (typically collected in volumes between 1-10 mL, 5-10 mL or greater) may be initially liquefied to reduce its viscosity and heterogeneity for consistent sample processing. Sputum samples present a particular challenge. MTB in sputum is one of the most challenging cell and sample types to process due to the lipid-rich hydrophobic cell wall of acid fast bacilli and the viscous, heterogeneous nature of sputum. Standard extraction methods for sputum typically start with a process of sedimentation, which often involves the treatment with a mucolytic agent such N-acetyl-L-cysteine (NALC), zephiran-trisodium phosphate (Z-TSP), or benzalkonium followed by centrifugation, decanting, and resuspension.

Accordingly, when processing highly viscous samples, such as sputum, the sample may be subjected to chemical treatment in order to reduce the viscosity so that subsequent processing steps) are not impeded. In one embodiment, liquefaction of sputum samples by chemical treatment with mucolytic agents is carried out for 20 minutes at 60° C. Sputum has a viscosity range from about 100-6,000 cP (mPas) with a shear rate at 90 s-1. The viscosity, measured in mPas, is determined by shear strength divided by shear rate. Preferably, the sample is liquefied to reduce the viscosity of sputum by at least 50%, at least 60%, at least 70%, at least 80%, at least 90%, at least 95%, or at least 99%.

Following resuspension, the sample is added to a bead beating system (as described in Section 4.1) of the disclosure for cell lysis, as described in Section 4.4. Following lysis and nucleic acid extraction (see Section 4.5), MTB DNA can be analyzed by PCR amplification of MTB sequences and MTB drug resistance can be analyzed by amplification of drug resistance genes. Sputum samples can be analyzed for other bacterial and viral pathogens, including but not limited to, *Staphylococcus aureus*, methicillin resistant *Staphylococcus aureus* (MRSA), *Streptococcus pyogenes*, *Streptococcus pneumoniae*, *Streptococcus agalactiae*, *Haemophilus influenzae*, *Haemophilus parainfuluezae*, *Moraxella catarrhalis*, *Klebsiella pneumoniae*, *Escherichia coli*, *Pseudomonas aeruginosa*, *Acinetobacter* sp., *Bordetella pertussis*, *Neisseria meningitidis*, *Bacillus anthracis*, *Nocardia* sp., *Actinomyces* sp., *Mycoplasma pneumoniae*, *Chlamydia pneumonia*, *Legionella* species, *Pneumocystis jiroveci*, influenza A virus, cytomegalovirus, and rhinovirus.

6.2 Use of Bead-Beating to Recover DNA from Veterinary Pathogens

*Mycobacterium avium* subsp paratuberculosis (MAP) is a veterinary pathogen that is responsible for causing paratuberculosis or Johne's disease (JD), a chronic granulomatous gastroenteritis in domestic and wild ruminants. MAP is transmitted in herds both directly through semen, milk, colostrum and in-utero and indirectly by oral route through contaminated feed, fodder, pasture, waters etc., (fecal oral route). JD has a devastating effect on the livestock productivity (early culling and reduced milk production) and livestock industry incurs huge economic losses. JD control efforts have been hampered by MAP's persistence within soil and water as well as shedding by subclinical and clinical cattle.

As mentioned in the preceding section, the formation of spores makes it challenging to lyse mycobacterial cells to extract bacterial DNA. Accordingly, the bead beating systems of the disclosure can be used to improve MAP recovery. For example, the bead beating systems can be used to recover DNA from MAP present in milk, soil, feces, semen, etc.

Milk samples can be directly processed using the bead beating systems of the disclosure or can be pre-processed, e.g., to increase the concentration of MAP, if present, in the sample. An exemplary pre-treatment method comprises centrifuging a sample of milk to provide a cream fraction, a whey fraction, and a pellet. The cream fraction and the pellet can be pooled and added to a bead beating system of the disclosure for cell lysis.

Fecal samples can be pre-processed, for example, by preparing fecal suspensions that can then be added to a bead beating system of the disclosure for cell lysis. An exemplary fecal suspension can be prepared by mixing a fecal sample with water, saline or a buffer (e.g., sodium phosphate, phosphate buffered saline, Tris, etc.), allowing the mixture to settle, separating and then centrifuging the supernatant and, finally, resuspending the pellet in a suitable liquid such as water, saline, or a buffer.

Soil samples can be suspended in a liquid (e.g., water, saline, or a buffer) and then added to a bead beating system of the disclosure for lysis. Semen samples can be similarly pre-processed by combining a semen sample with an amount of water, saline, or buffer prior to bead beating.

6.3 Use of Bead-Beating to Recover Pathogen DNA from Wounds

For detection of wound infections, a wound swab can be incubated in a solution of saline, a cell culture medium, or a sample preparation solution from a commercial kit. The swab is typically incubated for a period of approximately 5 minutes-1 hour and more preferably 0.25-1 hour (e.g., 0.25 hour, 0.5 hour or 0.75 hour). A suitable volume of solution is 200 μL to 10 mL and in particular embodiments is 500 μL, 1 mL, 2 mL, 5 mL, 8 mL or selected from a range bounded by any two of the foregoing embodiments, (e.g., 1 mL to 5 mL, 500 μl to 10 mL, 200 μL to 8 mL, and so on and so forth. The solution can be periodically shaken or agitated to promote the release of pathogenic cells from the swab. At the end of the incubation period the swab can be squeezed and discarded.

The solution can then be placed in a bead beating system of the disclosure. Optionally, it is filtered and/or concentrated prior to bead beating.

Pathogens that commonly infect wounds include, but are not limited *E. coli, P. aeruginosa, E faecium, S. aureus* (including MRSA), *K. pneumoniae, A. baumannii, C. amycolatum, E. aerogenes, E. faecalis* CI 4413, *S. marcescens, S. equi* and *C. albicans*. Accordingly, wound swab samples can be analyzed for any of the foregoing organisms, singly or in combination.

6.4 Use of Bead-Beating to Recover Pathogen DNA from Peritoneal Dialysis Fluid Peritoneal dialysis is a treatment for patients with severe chronic kidney disease. This type of dialysis uses the patient's peritoneum in the abdomen as a membrane across which fluids and dissolved substances are exchanged from the blood. Fluid is introduced through a permanent tube in the abdomen and then flushed out in order to clear excessive salts, uric acid and other waste substances. By osmosis across the peritoneal membrane, solutes are exchanged between the blood and the dialysis fluid. After a suitable time, the dialysis fluid is removed from the peritoneum and discarded. In this way, the blood becomes equilibrated and terminal metabolic products, such as uric acid, are prevented from indefinitely accumulating in the blood.

The primary complication of peritoneal dialysis is infection due to the presence of a permanent tube in the abdomen. At least one site of infection is in the peritoneal space, leading to abdominal pain, cloudy dialysis effluent and findings of pathogens on gram stains or in cultures from within the catheter. Further, the tissue tunnel or external surfaces of the catheter are common infection points from touch contamination. Infection at the tissue tunnel is most commonly due to migration from skin sites. Infections may lead to peritonitis and in some cases death.

Peritoneal infections can be detected in peritoneal dialysis fluid removed from individuals undergoing peritoneal dialysis. Although *S. aureus* and *P. aeruginosa* are responsible for the majority of infections, other bacteria (diphtheroids, anaerobic organisms, nonfermenting bacteria, streptococci, nontuberculous mycobacteria, *Legionella*, yeasts, and fungi) can also be involved. Accordingly, peritoneal dialysis fluid samples can be analyzed for any of the foregoing organisms, singly or in combination.

Peritoneal dialysis fluid can be pre-processed by filtration and optionally concentration as described in Section 4.3.

6.5 Use of Bead-Beating to Recover DNA from Wastewater Contaminants

Example 1 of U.S. Pat. No. 9,290,796, directed to the detection of problematic foaming and bulking bacterial species in biological wastewater treatment process, describes extracting DNA wastewater collected from wastewater treatment plants using a bead beating protocol. The bead-beating protocol can be adapted to incorporate a bead-beating system of the disclosure.

6.6 Use of Bead-Beating to Recover DNA from Food Pathogens

Liquid food samples can be pre-processed by filtration and/or centrifugation as described above in Section 4.3 prior to bead-beating. For example, drinks can preferably be pre-processed by filtration to collect microorganisms that may be present. The microorganisms collected by filtration can optionally be washed and subjected to centrifugation prior to bead-beating. For detection of pathogens from solid foods, such as meat or fish, a sample of the food can be swabbed to collect microorganisms from the surface of the food. The microorganisms can then be washed from the swab and then subjected to bead-beating.

In some cases, it can be desirable to pre-culture a food sample for a period of time in order to facilitate growth of pathogens (e.g., *Salmonella*) that may be present on or in the sample prior to bead-beating. For example, a solid food sample can be ground using a laboratory blender (e.g., a Stomacher® circulator, Seward Limited, UK) and then cultured to facilitate microorganism growth (e.g., for 8 to 12 hours). A sample of the culture can then be subjected to bead-beating.

6.7 Use of Bead-Beating to Recover Pathogen DNA from Blood

The development of rapid molecular diagnostic tests for human infections is the most highly rated priority of the World Health Organization for health improvement of the world population (Daar et al., 2002, Nat. Genet. 32:229-232). Severe blood infections are an important cause of morbidity and death in hospitalized patients worldwide and one of the most important challenges in critical care. For example, recent estimates of sepsis incidence are of 240 cases per 100 000 in the United States. The human and economic burden of sepsis is considerable (Grossi et al., 2006, Surg. Infect. (Larchmt) 7:S87-S91). Despite advances in infectious diseases and critical care management and numerous attempts to develop new treatments, sepsis mortality rate remains unacceptably high, ranging from 20% to 50%. Recognizing the signs of severe blood infections and/or severe sepsis and making an early and accurate diagnosis are the key to improving care and increasing the survival rate. Indeed, rapid diagnostics could increase patient survival by reducing the time interval between blood sampling and antimicrobial therapy application.

For molecular techniques of detecting pathogens (e.g., PCR and DNA sequence analysis), adequate isolation of pathogen DNA is critical to ensure successful detection. Various methods use lysis buffers, sometimes accompanied by physical disruption methods such as bead-beating, to improve recovery of pathogen DNA from blood.

The present disclosure takes advantage of the presence of naturally occurring blocking agents in blood and provides simplified methods for isolation of pathogen DNA from blood. The blood can be subject to bead beating without being diluted with any buffer or other additive, using a bead beating system of the disclosure (containing blocking agents) or a traditional bead beating system (lacking blocking agents). After bead beating, standard methods can be used to recover pathogen DNA, such as those described in Section 4.5. Optionally, the recovered pathogen DNA is then analyzed, for example by the methods described in Section 4.6.

Sepsis causing pathogens are typically bacterial or fungal. Common bacterial causes of sepsis are gram-negative bacilli (for example, *E. coli, P. aeruginosa, E. corrodens*, and *H. influenzae*). Other bacteria also causing sepsis are *S. aureus, Streptococcus* species, *Enterococcus* species and *Neisseria. Candida* species are some of the most frequent fungi that cause sepsis. Accordingly, blood samples can be analyzed for any of the foregoing organisms, singly or in combination.

7. EXAMPLES

7.1 Example 1: Bead Beating Systems Result in DNA Loss

7.1.1 Materials

The materials used in this study are:

Bead beating tube: part number: ARY0007 OPS Diagnostics, 4.5 mL cryovial, with 2.0 gm of 100 μm $SiO_2$ beads.

PD Fluid: Peritoneal dialysis fluid containing glucose and a balance of $Na^+$, $Ca^{2+}$, $Mg^{2+}$.

BE Buffer: Taigen Bioscience. Containing 1 μg of RNA/μl.

Urea: ACS grade

7.1.2 Methods

Two (2) mL of PD fluid spiked with EDTA at a level of 10 mM and C. albicans at 5000 CFU/mL was the standard matrix. Twelve (12) different combinations of urea and BE buffer were added to the sample, as shown in Table 1 below:

TABLE 1

Samples

| Sample no. | Sample | BE Buffer | Urea |
|---|---|---|---|
| 1 | PD fluid + EDTA + 5000 CFU/mL C.albicans | 0 | 0 |
| 2 | PD fluid + EDTA + 5000 CFU/mL C.albicans | 30 μl | 0 |
| 3 | PD fluid + EDTA + 5000 CFU/mL C.albicans | 75 μl | 0 |
| 4 | PD fluid + EDTA + 5000 CFU/mL C.albicans | 0 | 23.3 g/L |
| 5 | PD fluid + EDTA + 5000 CFU/mL C.albicans | 30 μl | 23.3 g/L |
| 6 | PD fluid + EDTA + 5000 CFU/mL C.albicans | 0 | 2.3 g/L |
| 7 | PD fluid + EDTA + 5000 CFU/mL C.albicans | 30 μl | 2.3 g/L |
| 8 | PD fluid + EDTA + 5000 CFU/mL C.albicans | 0 | 0.23 g/L |
| 9 | PD fluid + EDTA + 5000 CFU/mL C.albicans | 30 μl | 0.23 g/L |
| 10 | PD fluid + EDTA + 5000 CFU/mL C.albicans | 0 | 23.3 g/L |
| 11 | PD fluid + EDTA + 5000 CFU/mL C.albicans | 30 μl | 23.3 g/L |
| 12 | PD fluid + EDTA + 5000 CFU/mL C.albicans | 0 | 2.3 g/L |

All samples were bead beaten for 45 seconds. Following bead beating, DNA was isolated from the samples using the LabTurbo® 48 nucleic acid extraction system (Taigen Bioscience Corporation, Taipei, Taiwan) using the manufacturer's reagents and protocol. DNA isolated from 2.0 ml of each bead-beating sample was eluted in 100 μl of TE (Tris EDTA) buffer. The isolated DNA was subject to real time PCR amplification and quantification in order to determine the amount of target DNA in each sample.

7.1.3 Results

The optical density ratio (which is an indicator of the purity of the isolated DNA) and corresponding DNA concentration for each sample is shown in Table 2 below:

TABLE 2

DNA Recovery

| Sample no. | BE Buffer | Urea | A260/A280 | DNA conc. (ng/μL) |
|---|---|---|---|---|
| 1 | 0 | 0 | 1.97 | 5.5 |
| 2 | 30 μl | 0 | 3.02 | 54 |
| 3 | 75 μl | 0 | 3.16 | 125 |
| 4 | 0 | 23.3 g/L | 2.45 | 18.7 |
| 5 | 30 μl | 23.3 g/L | 3.09 | 53 |
| 6 | 0 | 2.3 g/L | 2.53 | 22 |
| 7 | 30 μl | 2.3 g/L | 2.97 | 48.7 |
| 8 | 0 | 0.23 g/L | 2.81 | 22.2 |
| 9 | 30 μl | 0.23 g/L | 3.05 | 51 |
| 10 | 0 | 23.3 g/L | 2.95 | 14.4 |
| 11 | 30 μl | 23.3 g/L | 3.01 | 56 |
| 12 | 0 | 2.3 g/L | 2.93 | 22 |

The yield of DNA as reflected by intensity of signal obtained from imaging of the signal from the array following PCR amplification and hybridization is graphically illustrated in FIG. 6 and FIG. 7.

7.1.4 Conclusion

In Sample 1, containing no blocking agent, the recovery of C. albicans DNA was only 5.5 ng/mL. The inclusion of urea as a blocking agent increased recovery 3-4 fold and the inclusion of RNA as a blocking agent increased recovery approximately 10-20 fold, and the yield approached the theoretical maximum. This increased recovery results in improvements in C. albicans PCR gene amplification.

7.2 Example 2: Extraction of DNA Using a Bead Beating System of the Disclosure

7.2.1 Preparation of a Bead Beating System of the Disclosure

A stock blocking agent solution comprising 250 mg/mL urea, 25 mg/mL tetrasodium salt of ethylenediaminetetraacid (EDTA), 125 mg/mL adenosine monophosphate, 125 mg/mL guanosine monophosphate, 125 mg/mL cytosine monophosphate, 125 mg/mL thymidine monophosphate and 75 mg/mL sodium lauroyl sarcosinate was prepared in TE (Tris/EDTA) buffer.

200 microliters of the stock solution was added to a 4.5- to 5-mL sample tube and taken to dryness by vacuum, resulting in the dried blocking agent being deposited in the lower region of the inner wall of the sample tube. The dried blocking agent is expected to be stable for at least one year.

2.0 grams of 100 micrometer silicon dioxide beads were then added to the sample tube.

7.2.2 Use of a Bead Beating System of the Disclosure 6 mL of urine and 6 mL of peritoneal dialysis fluid were filtered through a 0.4 micrometer sterile filter and then 10,000 colony-forming units per milliliter Staphylococcus aureus grown in a culture lab were added to the urine and peritoneal dialysis fluid filtrates.

2.9 mL of spiked urine and 2.9 mL of spiked peritoneal dialysis fluid were transferred to sample tubes prepared as described in Section 7.2.1 or to sample tubes containing 2.0 grams of 100 micrometer silicon dioxide beads but lacking the blocking agent.

The tubes were capped and clamped in an MPBio bead beater and run for 30 seconds at full power. The caps were removed and placed on the sample rack of a commercial DNA isolation device. 2 mL of each sample was taken out from each tube and DNA extraction agents were then added (LabTurbo®). DNA extraction was then performed. 100 microliters of DNA extract was obtained for each sample.

The amount of extracted S. aureus DNA in each sample was determined by real time polymerase chain reaction according to Gillespie, et al., 2005, "Simultaneous Detection of Mastitis Pathogens, Staphylococcus aureus, Streptococcus uberis, and Streptococcus agalactiae by Multiplex Real- Time Polymerase Chain Reaction," J. Dairy Sci. 88:3510-3518. 1 microliter of each DNA extract was amplified in a 20 microliter reaction.

The samples processed using sample tubes lacking the blocking agent had a cycle threshold value of 32 for urine and of 38 for peritoneal dialysis fluid, showing a low DNA recovery.

The samples processed using sample tubes with the blocking agent had a cycle threshold value of 31 for urine and a cycle threshold value of 32 for peritoneal dialysis fluid, showing an improved recovery for the peritoneal dialysis fluid under these conditions.

7.3 Example 3: Blood as a Blocking Agent

7.3.1 Overview

This study was performed in order to identify the optimal bead beating conditions for blood samples. Culture-negative blood samples were spiked with pathogens *S. aureus*, *E. coli* and *C. albicans*. A positive PCR control was run. The concentration (genomic copies) of this control was set as the theoretical 100% recovery of the introduced pathogen. This study demonstrated that is possible to extract DNA from blood pathogens using bead beating in the absence of additives such as buffers, detergents, etc.

7.3.2 Materials

The materials specifically used in the study are:

Bead beating tube: part number: ARY0007 OPS Diagnostics, 4.5 mL cryovial, with 2.0 gm of 100 μm $SiO_2$ beads.

Blood: culture negative from healthy donors

*S. aureus*, *E. coli* and *C. albicans* cultures: all ATCC sourced

7.3.3 Methods

A series of thirty-eight (38) spiked blood samples were prepared consisting of 3.0 mL of blood and 15 μL of saline cultures containing cultured pathogens. Nothing was added to each blood sample other than the saline culture containing the cultured pathogen. The beating tubes were processed using a FastPrep®-24 homogenizer (MP Biomedicals) at a speed of 6.5 m/s. DNA was then isolated from the samples using the LabTurbo® 48 nucleic acid extraction system (Taigen Bioscience Corporation) using the manufacturer's reagents and protocol. DNA was amplified with 55 cycles of PCR and hybridized to an array which was then washed and imaged. The amounts of pathogens and bead beating times are shown in Table 3 below:

TABLE 3

| Sample no. | Sample | Beads/Tubes | Time |
| --- | --- | --- | --- |
| 1 | Blood/no spike | OPS/OPS | 45 |
| 2 | | | |
| 3 | Blood + 5000 CFU/mL *C. albicans* | OPS/OPS | 45 |
| 4 | | | |
| 5 | Blood + 5000 CFU/mL *C. albicans* | OPS/OPS | 50 |
| 6 | | | |
| 7 | Blood + 5000 CFU/mL *C. albicans* | OPS/OPS | 55 |
| 8 | | | |
| 9 | Blood + 5000 CFU/mL *C. albicans* | OPS/OPS | 60 |
| 10 | | | |
| 11 | Blood + 5000 CFU/mL *C. albicans* | OPS/OPS | 65 |
| 12 | | | |
| 13 | Blood + 5000 CFU/mL *S. aureus* | OPS/OPS | 45 |
| 14 | | | |
| 15 | Blood + 5000 CFU/mL *S. aureus* | OPS/OPS | 50 |
| 16 | | | |
| 17 | Blood + 5000 CFU/mL *S. aureus* | OPS/OPS | 55 |
| 18 | | | |
| 19 | Blood + 5000 CFU/mL *S. aureus* | OPS/OPS | 60 |
| 20 | | | |
| 21 | Blood + 5000 CFU/mL *S. aureus* | OPS/OPS | 65 |
| 22 | | | |
| 23 | Blood + 100000 CFU/mL *E. coli* | OPS/OPS | 45 |
| 24 | | | |
| 25 | Blood + 100000 CFU/mL *E. coli* | OPS/OPS | 50 |
| 26 | | | |
| 27 | Blood + 100000 CFU/mL *E. coli* | OPS/OPS | 55 |
| 28 | | | |
| 29 | Blood + 100000 CFU/mL *E. coli* | OPS/OPS | 60 |
| 30 | | | |
| 31 | Blood + 100000 CFU/mL *E. coli* | OPS/OPS | 65 |
| 32 | | | |
| 33 | Blood + 5000 CFU/mL *C. albicans* | MPBio/MPBio | 60 |
| 34 | | | |
| 35 | Blood + 5000 CFU/mL *S. aureus* | MPBio/MPBio | 60 |
| 36 | | | |
| 37 | Blood + 100000 CFU/mL *E. coli* | MPBio/MPBio | 60 |
| 38 | | | |

For the three different pathogens at the given spike level the genomic output per μl from the DNA isolation was calculated. This genomic copy value was used as the 100% efficiency target.

7.3.4 Results

Results are graphically illustrated in FIGS. 8 to 10, which show yield of DNA as reflected by intensity of signal obtained from imaging of the signal from the array following PCR amplification and hybridization. FIG. 8 presents the *C. albicans* times series along with the 100% target. FIG. 9 presents the *S. aureus* time series along with the 100% target. FIG. 10 presents the *E. coli* time series along with the 100% target.

7.3.5 Conclusion

For the three different pathogens, there was no evidence of signal loss due to pathogen DNA binding to the beads. In all cases at least 100% of theoretical was demonstrated. In 2 cases more the 100% was recovered, possibly due to the presence of DNA from dead bacteria in the spike.

8. SPECIFIC EMBODIMENTS

The present disclosure is exemplified by the specific embodiments below.

1. A bead beating system comprising (i) a sample tube having an inner cavity that is accessible by an aperture, (ii) beads, and (iii) a dry blocking agent, wherein the beads and dry blocking agent are located within the inner cavity of the sample tube.

2. The bead beating system of embodiment 1, wherein the blocking agent comprises one or more chaotropic agents, creatinine, one or more nucleotides, one or more oligonucleotides, or a combination thereof.

3. The bead beating system of embodiment 2, in which the blocking agent comprises one or more chaotropic agents comprising urea, one or more guanidine salts, one or more lithium salts, one or more magnesium salts, one or more detergents, or a combination thereof.

4. The bead beating system of embodiment 3, in which the blocking agent comprises one or more guanidine salts comprising guanidine isocyanate, guanidine chloride, or a combination thereof.

5. The bead beating system of embodiment 3 or embodiment 4, in which the blocking agent comprises one or more lithium salts comprising lithium perchlorate, lithium acetate, or a combination thereof.

6. The bead beating system of any one of embodiments 3 to 5, in which the blocking agent comprises magnesium chloride.

7. The beating system of any one of embodiments 3 to 6, in which the blocking agent comprises one or more detergents comprising sodium dodecyl sulfate, sodium laurosylfate sarcosinate, polyoxyethylene (20) sorbitan monolaurate, or a combination thereof.

8. The bead beating system of any one of embodiments 2 to 7, in which the blocking agent comprises one or more nucleotides comprising naturally occurring nucleotides, non-naturally occurring nucleotides, or a combination thereof.

9. The bead beating system of embodiment 8, in which the one or more nucleotides comprise one or more naturally occurring deoxyribonucleotides, one or more naturally occurring ribonucleotides, or a combination thereof.

10. The bead beating system of embodiment 9, in which the blocking agent comprises one or more deoxyribonucleotides comprising deoxyadenosine monophosphate, deoxyguanosine monophosphate, deoxycytosine monophosphate, deoxythymidine monophosphate, or a combination thereof.

11. The bead beating system of embodiment 9 or embodiment 10, in which the blocking agent comprises one or more ribonucleotides comprising adenosine monophosphate, guanosine monophosphate, cytosine monophosphate, thymidine monophosphate, or a combination thereof.

12. The bead beating system of any one of embodiments 2 to 11, in which the blocking agent comprises one or more oligonucleotides comprising ribonucleotides, deoxyribonucleotides, nucleotide analogs, or a combination thereof.

13. The bead beating system of embodiment 12, in which the blocking agent comprises one or more oligonucleotides each of which is independently 2 to 120 nucleotides long, 2 to 100 nucleotides long, 2 to 50 nucleotides long, 2 to 25 nucleotides long, 5 to 40 nucleotides, 2 to 15 nucleotides long, 8 to 120 nucleotides long, 8 to 80 nucleotides long, 10 to 100 nucleotides long, 15 to 50 nucleotides long, 50 to 100 nucleotides long, or 100 to 120 nucleotides long.

14. The bead beating system of embodiment 12 or embodiment 13, in which the oligonucleotides comprise DNA and/or RNA.

15. The bead beating system of any one of embodiments 1 to 14, in which the inner cavity of the sample tube is at least partially coated with a layer or film of the blocking agent.

16. The bead beating system of any one of embodiments 1 to 15, in which some or all of the beads are partially or fully coated with a layer or film of the blocking agent.

17. The bead beating system of any one of embodiments 1 to 16, comprising a powder containing the blocking agent.

18. The bead beating system of embodiment 17, wherein the powder is a lyophilized powder containing the blocking agent.

19. The bead beating system of any one of embodiments 1 to 18, wherein the beads are adapted to lyse bacteria, yeast, filamentous fungi, spores, plant cells, or animal cells.

20. The bead beating system of any one of embodiments 1 to 19, wherein the beads comprise mineral beads, ceramic beads, glass beads, metal beads, or a combination thereof.

21. The bead beating system of embodiment 20, wherein the beads comprise zirconium beads, zircon beads, zirconia beads, quartz beads, aluminum oxide beads, silicon carbide beads, ceramic beads, silicon dioxide glass beads, stainless steel beads, chrome steel beads, or a combination thereof.

22. The bead beating system of any one of embodiments 1 to 21, in which the beads have a diameter ranging from 50 μm to 3 mm.

23. The bead beating system of any one of embodiments 1 to 22, further comprising ethylenediaminetetraacetic acid (EDTA) and/or a sodium salt thereof located within the inner cavity of the sample tube.

24. The bead beating system of any one of embodiments 1 to 22, further comprising creatinine located within the inner cavity of the sample tube.

25. A method for lysing cells (e.g., to extract nucleic acids from the cells) contained in a liquid sample, comprising agitating the liquid sample within the sample tube of the bead beating system according to any one of embodiments 1 to 24 under conditions sufficient to lyse the cells.

26. A method for lysing cells (e.g., to extract nucleic acids from the cells) contained in a liquid sample containing an exogenous blocking agent, comprising agitating the liquid sample within a bead beating system comprising a bead beating tube and beads in the absence of lysis buffer and/or additives.

27. A method for lysing cells (e.g., to extract nucleic acids from the cells) contained in a liquid sample that has not been incubated with lysis buffer, comprising agitating the liquid sample and one or more blocking agents within a bead beating system comprising a bead beating tube and beads, optionally wherein the one or more blocking agents is a blocking agent present in a bead beating tube of any one of embodiments 1 to 24.

28. The method of embodiment 26 or embodiment 27, wherein the beads are adapted to lyse bacteria, yeast, filamentous fungi, spores, plant cells, or animal cells.

29. The method of any one of embodiments 26 to 28, wherein the beads comprise mineral beads, ceramic beads, glass beads, metal beads, or a combination thereof.

30. The method of embodiment 29, wherein the beads comprise zirconium beads, zircon beads, zirconia beads, quartz beads, aluminum oxide beads, silicon carbide beads, ceramic beads, silicon dioxide glass beads, stainless steel beads, chrome steel beads, or a combination thereof.

31. The method of any one of embodiments 26 to 30, in which the beads have a diameter ranging from 50 μm to 3 mm.

32. The method of any one of embodiments 25 to 26, further comprising a step of placing the liquid sample within the sample tube prior to agitating the liquid sample.

33. The method of embodiment 25 or embodiment 32, wherein the agitating comprises subjecting the bead beating system to an oscillating motion.

34. The method of any one of embodiments 25 to 33, wherein the sample is a biological sample, an environmental sample, or a food product.

35. The method of embodiment 34, wherein the sample is a biological sample selected from blood, serum, saliva, urine, gastric fluid, digestive fluid, tears, stool, semen, vaginal fluid, interstitial fluid, fluid derived from tumorous tissue, ocular fluid, sweat, mucus, earwax, oil, glandular secretions, breath, spinal fluid, hair, fingernails, skin cells, plasma, fluid obtained from a nasal swab, fluid obtained from a nasopharyngeal wash, cerebrospinal fluid, a tissue sample, fluid or tissue obtained from a throat swab, fluid or tissue obtained from a wound swab, biopsy tissue, placental fluid, amniotic fluid, peritoneal dialysis fluid, cord blood, lymphatic fluids, cavity fluids, sputum, pus, microbiota, meconium, breast milk, or a sample processed, extracted or fractionated from any of the foregoing.

36. The method of embodiment 35, wherein the biological sample is urine, sputum or a sample processed, extracted or fractionated from urine.

37. The method of embodiment 35, wherein the biological sample is sputum or a sample processed, extracted or fractionated from sputum.

38. The method of embodiment 35, wherein the biological sample is a wound swab or a sample processed, extracted or fractionated from a wound swab.

39. The method of embodiment 35, wherein the biological sample is blood or a sample processed, extracted or fractionated from blood.

40. The method of embodiment 35, wherein the biological sample is peritoneal dialysis fluid or a sample processed, extracted or fractionated from peritoneal dialysis fluid.

41. The method of embodiment 34, wherein the sample is an environmental sample selected from soil, groundwater, surface water, wastewater, or a sample processed, extracted or fractionated from any of the foregoing.

42. The method of any one of embodiments 25 to 41, wherein the cells comprise one or more pathogens.

43. The method of embodiment 42, wherein the one or more pathogens comprise one or more bacterial pathogens, viral pathogens, fungal pathogens, or a combination thereof.

44. The method of embodiment 42 or embodiment 43, wherein the one or more pathogens comprise one or more of *Mycobacterium tuberculosis, Mycobacterium avium* subsp *paratuberculosis, Staphylococcus aureus,* methicillin resistant *Staphylococcus aureus* (MRSA), *Streptococcus pyogenes, Streptococcus pneumoniae, Streptococcus agalactiae, Haemophilus influenzae, Haemophilus parainfuluezae, Moraxella catarrhalis, Klebsiella pneumoniae, Escherichia coli, Pseudomonas aeruginosa, Acinetobacter* sp., *Bordetella pertussis, Neisseria meningitidis, Bacillus anthracis, Nocardia* sp., *Actinomyces* sp., *Mycoplasma pneumoniae, Chlamydia pneumonia, Legionella species, Pneumocystis jiroveci,* influenza A virus, cytomegalovirus, rhinovirus, *Enterococcus faecium, Acinetobacter baumannii, Corynebacterium amycolatum, Enterobacter aerogenes, Enterococcus faecalis* CI 4413, *Serratia marcescens, Streptococcus equi,* and *Candida albicans.*

45. The method of embodiment 42, in which the sample is sputum or a sample processed, extracted or fractionated from sputum and the one or more pathogens comprise one or more of *Mycobacterium tuberculosis, Staphylococcus aureus,* methicillin resistant *Staphylococcus aureus* (MRSA), *Streptococcus pyogenes, Streptococcus pneumoniae, Streptococcus agalactiae, Haemophilus influenzae, Haemophilus parainfuluezae, Moraxella catarrhalis, Klebsiella pneumoniae, Escherichia coli, Pseudomonas aeruginosa, Acinetobacter* sp., *Bordetella pertussis, Neisseria meningitidis, Bacillus anthracis, Nocardia* sp., *Actinomyces* sp., *Mycoplasma pneumoniae, Chlamydia pneumonia, Legionella* species, *Pneumocystis jiroveci,* influenza A virus, cytomegalovirus, and rhinovirus.

46. The method of embodiment 45, in which the one or more pathogens comprise *Mycobacterium tuberculosis.*

47. The method of embodiment 42, in which the sample is milk or semen, or a sample processed, extracted or fractionated from milk, soil, feces, or semen, and the one or more pathogens comprises *Mycobacterium avium* subsp paratuberculosis.

48. The method of embodiment 42, in which the sample is a wound swab or a sample processed, extracted or fractionated from a wound swab and the one or more pathogens comprise one or more of *E. coli, P. aeruginosa, E. faecium, S. aureus, K. pneumoniae, A. baumannii, C. amycolatum, E. aerogenes, E. faecalis* CI 4413, *S. marcescens, S. equi* and *C. albicans.*

49. The method of embodiment 42, in which the sample is peritoneal dialysis fluid or a sample processed, extracted or fractionated from peritoneal dialysis fluid and the one or more pathogens comprise *S. aureus* and/or *P. aeruginosa.*

50. The method of any one of embodiments 25 to 49, wherein the liquid sample comprises cells from multiple species.

51. The method of any one of embodiments 25 to 50, further comprising recovering the liquid sample from the sample tube following cell lysis.

52. The method of embodiment 51, further comprising purifying the nucleic acids from the recovered liquid sample.

53. The method of any one of embodiments 25 to 52, further comprising analyzing one or more of the nucleic acids.

54. The method of embodiment 53, wherein the analysis is performed using a microarray or by sequencing the one or more nucleic acids.

55. The method of embodiment 53 or embodiment 54, wherein a target sequence is amplified prior to performing the analysis.

56. The method of embodiment 55, wherein the target sequence is amplified by PCR.

57. The method of any one of embodiments 25 to 56, wherein the nucleic acids comprise DNA.

58. The method of any one of embodiments 25 to 57, wherein the nucleic acids comprise RNA.

59. A kit for lysing cells (e.g., to extract nucleic acids from the cells) contained in a liquid sample, comprising the bead beating system of any one of embodiments 1 to 24 and optionally: (i) one or more components for preparing the liquid sample, (ii) one or more oligonucleotides for amplifying one or more of the nucleic acids, (iii) one or more probes for detecting one or more of the nucleic acids, or (iv) any combination of (i) to (ii).

60. The kit of embodiment 59, which comprises one or more components for preparing the liquid sample, and wherein the one or more components for preparing the liquid sample comprise water, saline, a buffer, a filter, or a combination thereof.

61. The kit of embodiment 59 or embodiment 60, which comprises one or more oligonucleotides for amplifying one or more of the nucleic acids.

62. The kit of any one of embodiments 59 to 61, which comprises one or more probes for detecting one or more of the nucleic acids.

63. A kit for obtaining the bead beating system of any one of embodiments 1 to 24, comprising a sample tube, beads, and a dry blocking reagent.

64. The kit of embodiment 63, in which the beads and/or dry blocking reagent are included in the kit separately from the sample tube.

65. The kit of embodiment 63, in which the beads and/or dry blocking reagent are included in the kit within the sample tube.

66. The kit of any one of embodiments 63 to 65, further comprising one or more components for preparing a sample containing cells for nucleic acid extraction using the bead beating system, one or more oligonucleotides for amplifying one or more nucleic acids, one or more probes for detecting one or more nucleic acids, or a combination thereof.

67. A bead beating tube (1) comprising a sample tube comprising a container member (2) with an inner cavity (3), an aperture (4) for filling a sample fluid (5) potentially containing microorganisms into the inner cavity (3), and a closure (6) for closing the aperture (4), wherein a plurality of macroscopic, mineral particles (7) are arranged in the inner cavity (3) which are adapted to mechanically destroy the cell walls of the microorganisms contained in the sample fluid (5) when the sample fluid (5) is filled into the inner cavity (3) and the bead beating tube (1) is subject to mechanical oscillations, characterized in that a blocking agent (8) comprising urea and/or at least one guanidine salt and/or at least one detergent is arranged in dried form in the inner cavity (3) of the sample tube.

68. The bead beating tube (1) according to embodiment 67, characterized in that the blocking agent (8) comprises deoxyadenosine monophosphate, deoxyguanosine monophosphate, deoxycytosine monophosphate, deoxythymidine monophosphate, or a mixture of at least two of these monophosphates.

69. The bead beating tube (1) according to embodiments 67 or 68, characterized in that the blocking agent (8) comprises adenosine monophosphate, guanosine monophosphate, cytosine monophosphate, thymidine monophosphate, or a mixture of at least two of these monophosphates.

70. The bead beating tube (1) according to any of embodiments 67 to 69, characterized in that the at least one monophosphate contained in the blocking agent (8) is an oligonucleotide of at least 2 and at most 120 nucleotides.

71. The bead beating tube (1) according to any of embodiments 67 to 70, characterized in that the at least one detergent comprises sodium dodecyl sulfate, sodium lauroylsulfate sarcosinate and/or Polyoxyethylene (20) sorbitan monolaurate.

72. The bead beating tube (1) according to any of embodiments 67 to 71, characterized in that the dried blocking agent is arranged loosely in the inner cavity (3) of the container member (2), preferably in powdered form.

73. The bead beating tube (1) according to any of embodiments 67 to 72, characterized in that the inner wall of the container member (2) is at least partially coated with a layer or a film of the blocking agent.

74. The bead beating tube (1) according to any of embodiments 67 to 73, characterized in that ethylenediaminetetraacetic (EDTA) acid and/or a sodium salt thereof is arranged in the inner cavity (3) of the sample tube.

75. The bead beating tube (1) according to any of embodiments 67 to 74, characterized in that creatinine is arranged in the inner cavity (3) of the sample tube.

76. Use of a bead beating tube (1) according to any of embodiments 67 to 75 for extracting deoxyribonucleic acid and/or ribonucleic acid from microorganisms.

77. A method for extracting deoxyribonucleic acid and/or ribonucleic acid from microorganisms, wherein a sample fluid (5) is provided which is assumed to contain the microorganisms, wherein a plurality of mineral particles (7) movable relative to each other is introduced in the sample fluid (5) and the sample fluid (5) with the particles (7) contained therein is oscillated such that the particles (7) are capable of mechanically destroying cell walls of the microorganisms contained in the sample fluid (5), characterized in that a blocking agent (8) comprising urea and/or at least one guanidine salt and/or at least one detergent is introduced in the sample fluid (5) before and/or while the particles (7) are oscillated.

78. The method according to embodiment 77, characterized in that the amount of urea is aligned with the amount of the sample fluid (5) such that the concentration of the urea dissolved in the sample fluid (5) ranges between 10 and 100 grams per liter, in particular between 20 and 50 grams per liter, and preferably between 25 and 35 grams per liter.

79. The method according to embodiment 77 or 78, characterized in that, before and/or while the particles (7) are oscillated, at least one of the following monophosphates is introduced in the sample fluid (5): deoxyadenosine monophosphate, deoxyguanosine monophosphate, deoxycytosine monophosphate, deoxythymidine monophosphate.

80. The method according to any of embodiments 77 to 79, characterized in that, before and/or while the particles (7) are oscillated, at least one of the following monophosphates is introduced in the sample fluid (5): adenosine monophosphate, guanosine monophosphate, cytosine monophosphate, thymidine monophosphate.

81. The method according to any of embodiments 77 to 80, characterized in that creatinine and/or ethylenediaminetetraacetic acid (EDTA) and/or a sodium salt thereof are introduced in the sample fluid (5) before and/or while the particles (7) are oscillated.

9. CITATION OF REFERENCES

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there is an inconsistency between the teachings of one or more of the references incorporated herein and the present disclosure, the teachings of the present specification are intended.

9.1 Incorporation of EP16153540

The invention relates to a bead beating tube, comprising a sample tube comprising a container member with an inner cavity, an aperture for filling a sample fluid containing microorganisms into the inner cavity, and a closure for closing the aperture, wherein a plurality of macroscopic, mineral particles are arranged in the inner cavity which are adapted to mechanically destroy the cell walls of the microorganisms contained in the sample fluid when the sample fluid is filled into the inner cavity and the beat beating tube is subject to mechanical oscillations. The invention further relates to a method for extracting deoxyribonucleic acid (DNA) and/or ribonucleic acid (RNA) from microorganisms, wherein a sample fluid is provided which is assumed to contain the microorganisms, wherein a plurality of mineral particles movable relative to each other are introduced in the sample fluid and the sample fluid with the particles contained therein is oscillated such that the particles are capable of mechanically destroying cell walls of the microorganisms contained in the sample fluid.

Genetic testing and diagnosis of infectious diseases are playing an important role in the field of clinical microbiology. To overcome the bias and limitations inherent with cultivation-based methodologies, genetic testing is being increasingly used to detect microorganisms contained in a sample. In order that such genetic testing can be performed, the DNA and/or the RNA first of all have/has to be extracted from the microorganisms in a concentration as high as possible. In a method proposed by Zhongtang Yu et al. in "Improved extraction of PCR-quality community DNA from digesta and fecal samples", BioTechniques, Vol. 36, No. 5, p. 808-812 (May 2004), 0.25 g of a sample fluid taken from a cow's gastro-intestinal system are provided, which is assumed to contain microorganisms, namely bacteria. The sample fluid is first of all mixed with 1 mL of a buffer containing 500 mM sodium chloride, 50 mM Tris hydrochloride, pH 8.0, 50 mM ethylenediaminetetraacetic acid, and 4% sodium dodecyl sulfate. Moreover, 0.4 g sterile zircon beads are introduced in the sample fluid. The mixture thus obtained is subsequently oscillated by means of a Mini-BeadBeater™ in a sample tube for three minutes such that the beads destroy the cell walls of the microorganisms. In this process, the DNA contained in the cells is released. The buffer also serves to protect the DNA from degradation by DNases which are contained in the sample fluid.

After performing the bead beating, impurities are removed from the sample by precipitation with ammonium acetate. The nucleic acids are obtained by precipitation with isopropanol. In a further method step the DNA is digested sequentially with RNase and Proteinase K and subsequently purified by means of a column.

The method has the disadvantage that it is relatively complex. Since the sample fluid is diluted by the adding of the buffer, the DNA concentration in the sample decreases. Therefore, the method allows only a limited detection accuracy and sensitivity.

It is therefore an object to provide a bead beating tube and a method of the initially mentioned kind which enable deoxyribonucleic acids and/or ribonucleic acids to be extracted quickly and in an amount sufficient for detection from microorganisms contained in a sample fluid.

With respect to the beat beating tube this object is solved with the features of embodiment 1' described below. They provide that a blocking reagent which comprises urea and/or at least one guanidine salt and/or at least one detergent is arranged in dried form in the inner cavity of the sample tube.

Surprisingly, it has turned out that, when using such beat beating tube for the extraction of deoxyribonucleic acids (DNA) and/or ribonucleic acids (RNA) from microorganisms contained in a sample fluid, a larger extracting rate of DNA and/or RNA can be achieved than when using a corresponding bead beating tube which does not contain the blocking reagent. It is assumed that the blocking reagent blocks binding sites of the mineral particles contained in the inner cavity of the sample tube and thus prevents the binding of the DNA and/or RNA extracted from the microorganisms to these binding sites. After the removing of the particles from the sample fluid, which may, for instance be performed in that the particles deposit on the bottom of the sample tube and the sample fluid located above the particles is removed from the sample tube by means of a pipette or the like, a correspondingly high proportion of DNA and/or RNA contained in the sample tube will then result in the sample fluid. The at least one detergent blocks binding sites at the inner wall of the sample tube to and prevents ribonucleic (RNA) acid and/or deoxyribonucleic acid (DNA) to bind to these binding sites. This will also enable a high extraction rate of DNA and/or RNA.

Due to the presence of the blocking reagent it is even possible to renounce a dilution of the sample fluid with an extraction buffer before bead beating. The sample fluid is in this case only diluted with the blocking reagent which may be present in the sample fluid in considerably lower concentration than is typically an extraction buffer.

Mineral particles are crystalline particles, ceramic particles, and/or glasses. The particles are movable relative to each other when they are arranged in the sample fluid. The particles preferably comprise quartz particles and/or zircon particles. Such particles are cheaply available in large amounts and are chemically inert with respect to deoxyribonucleic acid or ribonucleic acid. Quartz and/or particles have a relatively high specific weight, are hard and may have sharp edges. Therefore, they are well suited to open cell membranes when exposed to mechanical vibrations.

The dried blocking reagent is long-term stable, i.e. the bead beating tube can be transported and stored without problems for a longer period without the blocking effect of the blocking reagent decreasing considerably. The dried blocking reagent may be arranged loosely in the inner cavity of the container member, and/or the inner wall of the container member may be coated with a layer or a film of the blocking reagent. The blocking reagent is preferably lyophilized.

By means of the bead beating tube in accordance with the invention it is possible to extract DNA and/or RNA from the microorganisms contained in the sample fluid in a concentration sufficient to directly examine the DNA and/or RNA microbiologically with per se known methods. This may in particular occur by contacting the sample fluid with receptors immobilized on a surface, which bind specifically to the DNA and/or RNA and/or to DNA and/or RNA components contained therein. The binding of the DNA and/or RNA and/or of the DNA and/or RNA components to the receptors may be detected in a per se known manner by means of markers, in particular optical markers such as fluorescent dyes, and be quantified if necessary.

The at least one guanidine salt comprises preferably guanidine isocyanate and/or guanidine chloride.

In a preferred embodiment of the invention the blocking reagent comprises deoxyadenosine monophosphate, deoxyguanosine monophosphate, deoxycytosine monophosphate, deoxytymidine monophosphate, or a mixture of at least two of these monophosphates. These monophosphates can block binding sites of the particles which deoxyribonucleic acid (DNA) can bind to.

In a preferred embodiment of the invention the blocking reagent comprises adenosine monophosphate, guanosine monophosphate, cytosine monophosphate, thymidine monophosphate, or a mixture of at least two of these monophosphates. These monophosphates can block binding sites of the particles which ribonucleic acid (RNA) can bind to. Ribonucleic acids are easier to degrade than deoxyribonucleic acid and are therefore better suited for a sample preparation.

It is of advantage if the at least one monophosphate contained in the blocking reagent is an oligonucleotide of at least 2 and at most 120 for example RNA and/or DNA nucleotides. The at least one monophosphate is then easy to produce synthetically.

In an expedient embodiment of the invention the at least one detergent comprises sodium-dodecylsulafte, sodium lauroylsulfate sarcosinate and/or Polyoxyethylen-(20)-sorbitanmonolaurat. Polyoxyethylen-(20)-sorbitanmonolaurat is also known as polysorbat 20. This blocks binding sites at the inner wall of the sample tube to and prevents ribonucleic acid and/or deoxyribonucleic acid to bind to these binding sites.

In an advantageous embodiment of the invention the dried blocking reagent is arranged loosely in the inner cavity of the container member, preferably in powdered form. The powder can be mixed with the particles.

In a preferred embodiment of the invention the inner wall of the container member is at least partially coated with a layer or a film of the blocking reagent. The blocking reagent is then captively connected with the container member.

It is of advantage if creatinine is arranged in the inner cavity of the sample tube. The presence of the creatinine in the inner cavity of the sample tube counteracts degradation of deoxyribonucleic acids and of ribonucleic acids contained in the sample fluid. Furthermore, the creatinine prevents that the DNA and/or the RNA non-specifically binds to the particles and/or the inner wall of the sample tube. This enables larger yield when extracting DNA and/or RNA from microorganism contained in the sample fluid by means of the bead beating tube.

In an expedient embodiment of the invention ethylenediaminetetraacetic acid and/or a sodium salt thereof is arranged in the inner cavity of the sample tube. Ethylenediaminetetraacetic acid binds calcium, magnesium and iron and thus inactivates deoxyribonucleases and ribonucleases. This measure also counteracts degradation of deoxyribonucleic acids and of ribonucleic acids contained in the sample fluid. Thus, higher detection sensitivity and reproducibility of the measurement results is enabled during an examination of deoxyribonucleic acid and/or ribonucleic acid extracted from microorganisms by means of the bead beating tubes in accordance with the invention.

With respect to the method the above-mentioned object is solved with the features of embodiment 11'. They provide that a blocking reagent which comprises urea, at least one guanidine salt and/or at least one detergent is introduced in the sample fluid before and/or while the particles are oscillated.

In a preferred embodiment of the invention the amount of urea is aligned with the amount of the sample fluid such that the concentration of the urea dissolved in the sample fluid ranges
between 10 and 100 grams per liter, in particular
between 20 and 50 grams per liter, and preferably
between 25 and 35 grams per liter.

This enables high yield when extracting the deoxyribonucleic acid and/or the ribonucleic acid.

In a preferred embodiment of the invention the amount of detergent is aligned with the amount of the sample fluid such that the concentration of the detergent dissolved in the sample fluid is between 1 and 50 mg/ml.

In the following, embodiments of the invention will be explained in detail by means of the drawing.

A bead beating tube designated with 1 in FIGS. 1 to 3 comprises a sample tube comprising a container member 2 with an inner cavity 3 and a closable aperture 4. The sample tube is preferably made of plastics, but may also be made of another biologically inert material.

A sample fluid 5 which is assumed to contain microorganisms may be filled into the inner cavity 3 of the container member 2 and removed therefrom through the aperture 4. For closing the aperture 4 the sample tube has a closure 6 adapted to be conveyed to an open and a closed position and being designed as a closure cap comprising an inner thread which is adapted to be screwed with an outer thread provided on the edge region of the outer wall of the container member 2 which bounds the aperture 4.

In the inner cavity 3, 2 grams of silicon dioxide are further arranged which comprise a plurality of particles 7 whose largest dimension is approximately 100 μm on average. The particles 7 are available in the form of a loose bulk in which they are movable relative to each other. Instead of the particles 7 of silicon dioxide or in addition thereto, zirconium particles of appropriate size may also be contained in the inner cavity 3.

The particles 7 serve to mechanically destroy the cell walls of the microorganisms contained in the sample fluid 5 when the sample fluid 5 is filled into the inner cavity and the bead beating tube is subject to mechanical oscillations, for instance, ultrasonic oscillations. They may be generated with an oscillation generator which is not illustrated in detail in the drawing and may be transferred to the bead beating tube 1. Such oscillation generator is commercially available under the designation MPBio bead beater with the Company MP Biomedicals. Due to the destroying of the cell walls the deoxyribonucleic acid contained in the microorganisms is released and dissolved in the sample fluid 5.

In the inner cavity 3 of the tube 1 a lyophilized blocking reagent 8 is also arranged, which is prepared as follows:

5 milligram tetrasodium salt of ethylenediaminetetraacid ($Na_4$-EDTA), 25 milligram adenosinmonophosphat, 25 milligram guanosinmonophosphat, 25 milligram cyotsinmonophosphat, 25 milligram thymidinmonophosphat and 15 mg sodium lauroyl sarcosinate are provided. In order to have these regents stable they are dissolved in TE buffer in a 5× concentration. For reason of solubility the tetrasodium salt of ethylenediaminetetraacid is used as this dissolves well in water. 1 milliliter then consists of 250 milligram Urea, 25 milligram tetrasodium salt of ethylenediaminetetraacid, 125 milligram adenosinmonophosphat, 125 milligram guanosinmonophosphat, 125 milligram cyotsinmonophosphat, 125 milligram thymidinmonophosphat and 75 mg sodium lauroyl sarcosinate.

200 microliter of this solution is put in the container member 2 and taken to dryness by vacuum. The dried in blocking reagent 8 is stable for at least one year. As can be seen in FIG. 4, the blocking reagent 8 is applied on the inner wall of the container member 2 as a thin layer in a lower partial region of the inner cavity 3 which is spaced apart from the aperture 4.

EMBODIMENT 6 milliliter urine and peritoneal dialysis fluid are filtered through a 0.4 micrometer sterile filter and then 10,000 colony-forming units per milliliter *Staphylococcus aureus* grown in a culture lab are added.

Method of the Invention:

2.9 milliliter spiked urine and spiked peritoneal dialysis fluid are transferred in the tube 1 described above. The tube is sealed by the screw cap 6 and clamped in an MPBio bead beater and run for 30 seconds at full power. The closure 6 is removed and placed on the sample rack of a commercial DNA isolation device. 2 milliliter of each sample are taken out and DNA extraction agents are then added (labturbo) and DNA extraction is performed. 100 microliter of DNA extract were produced.

Standard Method:

2.9 milliliter spiked urine and spiked peritoneal dialysis fluid are transferred in a tube for bead beating with 2.0 gram of 100 micrometer silica ($SiO_2$) beads. The tube does not contain the blocking reagent 8 and no further reagent are added. The tube is sealed by a closure and clamped in the MPBio bead beater and run for 30 seconds at full power. The closure is removed and placed on the sample rack of a commercial DNA isolation device. 2 milliliter of each sample are taken out and DNA extraction agents are then added (labturbo) and DNA extraction is performed. 100 microliter of DNA extract were produced.

Detection of the Extracted DNA

The amount of extracted *Staphylococcus aureus* DNA is determined by real time polymerase chain reaction according to Gillespie, G. E. et al.: "Simultaneous Detection of Mastitis Pathogens, *Staphylococcus aureus*, *Streptococcus*

*uberis*, and *Streptococcus agalactiae* by Multiplex Real-Time Polymerase Chain Reaction", J. Dairy Sci. 88:3510-3518 (2005). 1 microliter of extracted DNA was amplified in a 20 microliter reaction. The Standard method produced a cycle threshold value of 32 for urine and of 38 for peritoneal dialysis fluid showing a bad DNA recovery.

The method of the invention produced a cycle threshold value of 31 for urine and a cycle threshold value of 32 for peritoneal dialysis fluid showing a much better recovery for the peritoneal dialysis fluid under these conditions.

The disclosure is exemplified by the specific embodiments below.

1'. A bead beating tube (1) comprising a sample tube comprising a container member (2) with an inner cavity (3), an aperture (4) for filling a sample fluid (5) potentially containing microorganisms into the inner cavity (3), and a closure (6) for closing the aperture (4), wherein a plurality of macroscopic, mineral particles (7) are arranged in the inner cavity (3) which are adapted to mechanically destroy the cell walls of the microorganisms contained in the sample fluid (5) when the sample fluid (5) is filled into the inner cavity (3) and the bead beating tube (1) is subject to mechanical oscillations, characterized in that a blocking reagent (8) comprising
urea and/or
at least one guanidine salt and/or
at least one detergent
is arranged in dried form in the inner cavity (3) of the sample tube.

2'. The bead beating tube (1) according to embodiment 1', characterized in that the blocking reagent (8) comprises
deoxyadenosine monophosphate,
deoxyguanosine monophosphate,
deoxycytosine monophosphate,
deoxytymidine monophosphate,
or a mixture of at least two of these monophosphates.

3'. The bead beating tube (1) according to embodiments 1' or 2', characterized in that the blocking reagent (8) comprises
adenosine monophosphate,
guanosine monophosphate,
cytosine monophosphate,
thymidine monophosphate,
or a mixture of at least two of these monophosphates.

4'. The bead beating tube (1) according to any of embodiments 1' to 3', characterized in that the at least one monophosphate contained in the blocking reagent (8) is an oligonucleotide of at least 2 and at most 120 nucleotides.

5'. The bead beating tube (1) according to any of embodiments 1' to 4', characterized in that the at least one detergent comprises sodium-dodecylsulafte, sodium lauroylsulfate sarcosinate and/or Polyoxyethylen-(20)-sorbitanmonolaurat.

6'. The bead beating tube (1) according to any of embodiments 1' to 5', characterized in that the dried blocking reagent is arranged loosely in the inner cavity (3) of the container member (2), preferably in powdered form.

7'. The bead beating tube (1) according to any of embodiments 1' to 6', characterized in that the inner wall of the container member (2) is at least partially coated with a layer or a film of the blocking reagent.

8'. The bead beating tube (1) according to any of embodiments 1' to 7', characterized in that ethylenediaminetetraacetic acid and/or a sodium salt thereof is arranged in the inner cavity (3) of the sample tube.

9'. The bead beating tube (1) according to any of embodiments 1' to 8', characterized in that creatinine is arranged in the inner cavity (3) of the sample tube.

10'. Use of a bead beating tube (1) according to any of embodiments 1' to 9' for extracting deoxyribonucleic acid and/or ribonucleic acid from microorganisms.

11'. A method for extracting deoxyribonucleic acid and/or ribonucleic acid from microorganisms, wherein a sample fluid (5) is provided which is assumed to contain the microorganisms, wherein a plurality of mineral particles (7) movable relative to each other is introduced in the sample fluid (5) and the sample fluid (5) with the particles (7) contained therein is oscillated such that the particles (7) are capable of mechanically destroying cell walls of the microorganisms contained in the sample fluid (5), characterized in that a blocking reagent (8) comprising
urea and/or
at least one guanidine salt and/or
at least one detergent
is introduced in the sample fluid (5) before and/or while the particles (7) are oscillated.

12'. The method according to embodiment 11', characterized in that the amount of urea is aligned with the amount of the sample fluid (5) such that the concentration of the urea dissolved in the sample fluid (5) ranges
between 10 and 100 grams per liter, in particular
between 20 and 50 grams per liter, and preferably
between 25 and 35 grams per liter.

13'. The method according to embodiment 11' or 12', characterized in that, before and/or while the particles (7) are oscillated, at least one of the following monophosphates is introduced in the sample fluid (5):
deoxyadenosine monophosphate,
deoxyguanosine monophosphate,
deoxycytosine monophosphate,
deoxytymidine monophosphate.

14'. The method according to any of embodiments 11' to 13', characterized in that, before and/or while the particles (7) are oscillated, at least one of the following monophosphates is introduced in the sample fluid (5):
adenosine monophosphate,
guanosine monophosphate,
cytosine monophosphate,
thymidine monophosphate.

15'. The method according to any of embodiments 11' to 14', characterized in that creatinine and/or ethylenediaminetetraacetic acid and/or a sodium salt thereof are introduced in the sample fluid (5) before and/or while the particles (7) are oscillated.

What is claimed is:

1. A method for producing a lysate from cells contained in a blood sample, comprising agitating the blood sample within a bead beating system in the absence of a buffer, in the absence of a detergent, and in the presence of one or more endogenous blocking agents comprising urea under conditions sufficient to (i) lyse both a fungal pathogen and a bacterial pathogen and (ii) provide a lysate suitable for PCR amplification of DNA from the fungal pathogen, when present, and the bacterial pathogen, when present, said bead beating system comprising a bead beating tube and beads.

2. The method of claim 1, wherein the agitating is carried out in the absence of any additives.

3. The method of claim 1, wherein the beads:
a) are adapted to lyse yeast or filamentous fungi;
b) comprise:
   i. mineral beads, ceramic beads, glass beads, metal beads, or a combination thereof;

ii. zirconium beads, zircon beads, zirconia beads, quartz beads, aluminum oxide beads, silicon carbide beads, ceramic beads, silicon dioxide glass beads, stainless steel beads, chrome steel beads, or a combination thereof;

c) have a diameter ranging from 50 µm to 3 mm; or d) any combination of a)-c).

4. The method of claim 1, further comprising a step of placing the blood within the bead beating tube prior to agitating the blood.

5. The method of claim 1, which comprises agitating the blood under conditions sufficient to (i) lyse *Candida albicans* and (ii) provide a lysate suitable for PCR amplification of DNA from *Candida albicans*, when the *Candida albicans* is present.

6. The method of claim 1, which comprises agitating the blood under conditions sufficient to (i) lyse *Staphylococcus aureus* and (ii) provide a lysate suitable for PCR amplification of DNA from *Staphylococcus aureus*, when the *Staphylococcus aureus* is present.

7. The method of claim 5, which comprises agitating the blood under conditions sufficient to (i) lyse *Staphylococcus aureus* and (ii) provide a lysate suitable for PCR amplification of DNA from *Staphylococcus aureus*, when the *Staphylococcus aureus* is present.

8. The method of claim 1, which comprises agitating the blood under conditions sufficient to (i) lyse *Escherichia coli* and (ii) provide a lysate suitable for PCR amplification of DNA from *Escherichia coli*, when the *Escherichia coli* is present.

9. The method of claim 5, which comprises agitating the blood under conditions sufficient to (i) lyse *Escherichia coli* and (ii) provide a lysate suitable for PCR amplification of DNA from *Escherichia coli*, when the *Escherichia coli* is present.

10. The method of claim 6, which comprises agitating the blood under conditions sufficient to (i) lyse *Escherichia coli* and (ii) provide a lysate suitable for PCR amplification of DNA from *Escherichia coli*, when the *Escherichia coli* is present.

11. The method of claim 7, which comprises agitating the blood under conditions sufficient to (i) lyse *Escherichia coli* and (ii) provide a lysate suitable for PCR amplification of DNA from *Escherichia coli*, when the *Escherichia coli* is present.

12. The method of claim 1, wherein the agitating comprises subjecting the bead beating system to an oscillating motion.

13. The method of claim 12, wherein the agitating comprises subjecting the bead beating system to 2000 or more oscillations per minute.

14. The method of claim 1, wherein the agitating is performed with a vortexer or a homogenizer.

15. The method of claim 14, wherein the agitating is performed with a homogenizer.

16. The method of claim 15, wherein the agitating is performed for 25-60 seconds.

17. The method of claim 15, wherein the agitating is performed for 1-2 minutes.

18. The method of claim 1, wherein the blood comprises one or more pathogens.

19. The method of claim 18, wherein the one or more pathogens comprise one or more bacterial pathogens, viral pathogens, fungal pathogens, or a combination thereof.

20. The method of claim 19, wherein the one or more pathogens comprise *Candida albicans*.

21. The method of claim 19, wherein the one or more pathogens comprise *Staphylococcus aureus*.

22. The method of claim 19, wherein the one or more pathogens comprise *Escherichia coli*.

23. The method of claim 1, wherein the blood comprises cells from multiple species.

24. The method of claim 1, further comprising recovering the lysate from the bead beating tube following cell lysis.

25. The method of claim 24, further comprising purifying nucleic acids from the lysate.

26. The method of claim 1, further comprising analyzing one or more nucleic acids from the lysate.

27. The method of claim 26, wherein the analyzing comprises PCR to amplify DNA from the fungal pathogen, when present, and DNA from the bacterial pathogen, when present.

28. The method of claim 27, further comprising using a microarray to analyze the one or more nucleic acids or sequencing the one or more nucleic acids following PCR.

\* \* \* \* \*